(12) United States Patent
Kobayashi et al.

(10) Patent No.: US 11,065,429 B2
(45) Date of Patent: Jul. 20, 2021

(54) METHOD OF PRODUCING MICRONEEDLE ARRAY UNIT

(71) Applicant: FUJIFILM Corporation, Tokyo (JP)

(72) Inventors: Yuka Kobayashi, Kanagawa (JP); Yasuhiro Sekizawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/070,910

(22) Filed: Oct. 14, 2020

(65) Prior Publication Data

US 2021/0023356 A1  Jan. 28, 2021

Related U.S. Application Data

(63) Continuation of application No. PCT/JP2019/015645, filed on Apr. 10, 2019.

(30) Foreign Application Priority Data

May 8, 2018 (JP) .............................. JP2018-090129

(51) Int. Cl.
*B81B 1/00* (2006.01)
*B81C 1/00* (2006.01)
(Continued)

(52) U.S. Cl.
CPC ........ *A61M 37/0015* (2013.01); *B23P 11/005* (2013.01); *B65B 5/045* (2013.01);
(Continued)

(58) Field of Classification Search
CPC ....................... B81C 1/00111; B81B 2201/055
See application file for complete search history.

(56) References Cited

U.S. PATENT DOCUMENTS 9,492,647 B2  11/2016  Stumber et al.
9,789,299 B2  10/2017  Simmers
(Continued)

FOREIGN PATENT DOCUMENTS

CN  103170055  6/2013
CN  104797287  7/2015
(Continued)

OTHER PUBLICATIONS

"International Search Report (Form PCT/ISA/210) of PCT/JP2019/015645," dated May 28, 2019, with English translation thereof, pp. 1-2.
(Continued)

*Primary Examiner* — Moazzam Hossain
(74) *Attorney, Agent, or Firm* — JCIPRNET

(57) ABSTRACT

Provided is a method of producing a microneedle array unit which is capable of suppressing damage to a microneedle array. The method of producing a microneedle array unit, including an array preparing step of preparing a microneedle array which includes a sheet and a plurality of needles arranged on one surface of the sheet; a container preparing step of preparing a container which includes an accommodating portion defining an opening and a space for accommodating the microneedle array, and a deformable portion disposed on a side opposite to the opening and integrated with the accommodating portion; an accommodating step of accommodating the microneedle array in the accommodating portion of the container by allowing the other surface of the sheet of the microneedle array and the deformable portion of the container to oppose each other; and a deforming step of deforming an outer surface of the accommodating portion inward, which is positioned between the one surface of the sheet of the microneedle array and the opening (Continued)

of the accommodating portion, to form a protrusion that reduces an area of the opening.

12 Claims, 17 Drawing Sheets

(51) Int. Cl.
    *A61M 37/00*     (2006.01)
    *B23P 11/00*     (2006.01)
    *B65B 5/04*     (2006.01)

(52) U.S. Cl.
    CPC .......... *B81B 1/008* (2013.01); *B81C 1/00111* (2013.01); *A61M 2037/0053* (2013.01); *B81B 2201/055* (2013.01); *Y10T 29/49826* (2015.01)

(56) References Cited

U.S. PATENT DOCUMENTS

| | | |
|---|---|---|
| 9,937,336 B2 | 4/2018 | Yamada et al. |
| 10,406,339 B2 | 9/2019 | Simmers |
| 10,525,243 B2 | 1/2020 | Kato |
| 2008/0183144 A1* | 7/2008 | Trautman .......... A61M 37/0015 604/272 |
| 2016/0354589 A1* | 12/2016 | Kobayashi ........ A61M 37/0015 |
| 2018/0326193 A1 | 11/2018 | Kobayashi |

FOREIGN PATENT DOCUMENTS

| | | |
|---|---|---|
| CN | 105916543 | 8/2016 |
| CN | 106102818 | 11/2016 |
| JP | 2013013558 | 1/2013 |
| JP | 2013226427 | 11/2013 |
| JP | 5553612 | 7/2014 |
| JP | 2016131619 | 7/2016 |
| JP | 2018191783 | 12/2018 |
| WO | 2017061701 | 4/2017 |

OTHER PUBLICATIONS

"Written Opinion of the International Searching Authority (Form PCT/ISA/237) of PCT/JP2019/015645," dated May 28, 2019, with English translation thereof, pp. 1-8.

Office Action of China Counterpart Application, with English translation thereof, dated Apr. 6, 2021, pp. 1-17.

* cited by examiner

METHOD OF PRODUCING MICRONEEDLE ARRAY UNIT

CROSS-REFERENCE TO RELATED APPLICATIONS

The present application is a Continuation of PCT International Application No. PCT/JP2019/015645 filed on Apr. 10, 2019 claiming priority under 35 U.S.C § 119(a) to Japanese Patent Application No. 2018-090129 filed on May 8, 2018. Each of the above applications is hereby expressly incorporated by reference, in its entirety, into the present application.

BACKGROUND OF THE INVENTION

1. Field of the Invention

The present invention relates to a method of producing a microneedle array unit.

2. Description of the Related Art

In recent years, a microneedle array has been known as a new dosage form which enables administration of a drug into the skin without pain. The microneedle array is formed by arranging microneedles (also referred to as fine needles or micro-needles) containing a drug in an array. By pressing this microneedle array against the skin, the skin is punctured by each microneedle. The drug is absorbed into the skin from the microneedles that have punctured the skin and then administered.

A container, which is also referred to as an applicator, that protects a microneedle array until the skin is punctured by microneedles and enables the skin to be easily punctured by the microneedles in a state of accommodating the microneedle array has been suggested (JP5553612B).

SUMMARY OF THE INVENTION

Meanwhile, in a case where the microneedle array is accommodated in a container by applying a force thereto to attach the microneedle array to the applicator, such as fitting the microneedle array thereto, there is a concern that the microneedle array is damaged.

The present invention has been made in consideration of the above-described circumstances, and an object thereof is to provide a method of producing a microneedle array unit that is capable of suppressing damage to a microneedle array.

A method of producing a microneedle array unit according to a first aspect, comprising: an array preparing step of preparing a microneedle array which includes a sheet and a plurality of needles arranged on one surface of the sheet; a container preparing step of preparing a container which includes an accommodating portion defining an opening and a space for accommodating the microneedle array, and a deformable portion disposed on a side opposite to the opening and integrated with the accommodating portion; an accommodating step of accommodating the microneedle array in the accommodating portion of the container by allowing the other surface of the sheet of the microneedle array and the deformable portion of the container to oppose each other; and a deforming step of deforming an outer surface of the accommodating portion inward, which is positioned between the one surface of the sheet of the microneedle array and the opening of the accommodating portion, to form a protrusion that reduces an area of the opening of the accommodating portion.

According to the method of producing a microneedle array unit according to the first aspect, since the protrusion is formed after the microneedle array is accommodated in the container, damage to the microneedle array can be suppressed.

In the method of producing a microneedle array unit according to a second aspect, in the deforming step, two or more protrusions are formed. According to the second aspect, the microneedle array can be stably accommodated in the container.

In the method of producing a microneedle array unit according to a third aspect, in the accommodating step, the one surface of the sheet of the microneedle array is supported by a support having a hollow structure that defines an opening from below in a non-contact manner with the plurality of needles. According to the third aspect, the microneedle array can be supported without contacting the needles until the deforming step is completed.

In the method of producing a microneedle array unit according to a fourth aspect, the support has a notch extending downward from the opening of the support, and a part of the support having the notch is accommodated in the container, and the outer surface of the accommodating portion is deformed inward toward the notch using a pressing jig in the deforming step. According to the fourth aspect, the outer periphery of the accommodating portion can be locally deformed.

In the method of producing the microneedle array unit according to a fifth aspect, the microneedle array is accommodated in the container in a state in which the opening of the accommodating portion faces upward and the needles of the microneedle array face upward in the accommodating step, and the outer surface of the accommodating portion is deformed inward by a pressing jig in the deforming step. According to the fifth aspect, the microneedle array can be supported by the deformable portion until the deforming step is completed.

In the method of producing a microneedle array unit according to a sixth aspect, the pressing jig is heated. According to the sixth aspect, the deformation of the accommodating portion of the container can be promoted.

In the method of producing a microneedle array unit according to a seventh aspect, the microneedle array is sucked from the opening of the support. According to the seventh aspect, the microneedle array can be stably supported by the support.

In the method of producing a microneedle array unit according to an eighth aspect, the accommodating step and the deforming step are performed in a sterile environment. According to the eighth aspect, contamination of the microneedle array can be suppressed.

The method of producing a microneedle array unit according to a ninth aspect further comprises a sealing step of sealing the container after the deforming step. According to the ninth aspect, the microneedles can be protected until the skin is punctured by the microneedles by sealing the microneedle array unit.

In the method of producing a microneedle array unit according to a tenth aspect, the opening of the accommodating portion is sealed with a lid.

In the method of producing a microneedle array unit according to an eleventh aspect, the container is put in a bag and sealed. According to the tenth and eleventh aspects, the microneedle array unit can be easily sealed.

According to the present invention, it is possible to produce a microneedle array unit that is capable of suppressing damage to a microneedle array in a case of accommodating the microneedle array in a container.

DESCRIPTION OF THE PREFERRED EMBODIMENTS

Hereinafter, preferred embodiments of the present invention will be described with reference to the accompanying drawings. The present invention will be described based on the following preferred embodiments. Modifications can be made according to various techniques without departing from the scope of the present invention and other embodiments other than the embodiments can be used. Therefore, all modifications within the scope of the present invention are included in the scope of the appended claims. In the specification of the present application, "downward" indicates a direction of gravity, and "upward" indicates a direction opposite to the direction of gravity.

A method of producing a microneedle array unit according to an embodiment includes an array preparing step of preparing a microneedle array which includes a sheet and a plurality of needles arranged on one surface of the sheet; a container preparing step of preparing a container which includes an accommodating portion defining an opening and a space for accommodating the microneedle array, and a deformable portion disposed on a side opposite to the opening and integrated with the accommodating portion; an accommodating step of accommodating the microneedle array in the accommodating portion of the container by allowing the other surface of the sheet of the microneedle array and the deformable portion of the container to oppose each other; and a deforming step of deforming an outer surface of the accommodating portion inward, which is positioned between the one surface of the sheet of the microneedle array and the opening of the accommodating portion, to form a protrusion that reduces an area of the opening of the accommodating portion. The microneedle array unit comprises a container and a microneedle array.

Figure 1:
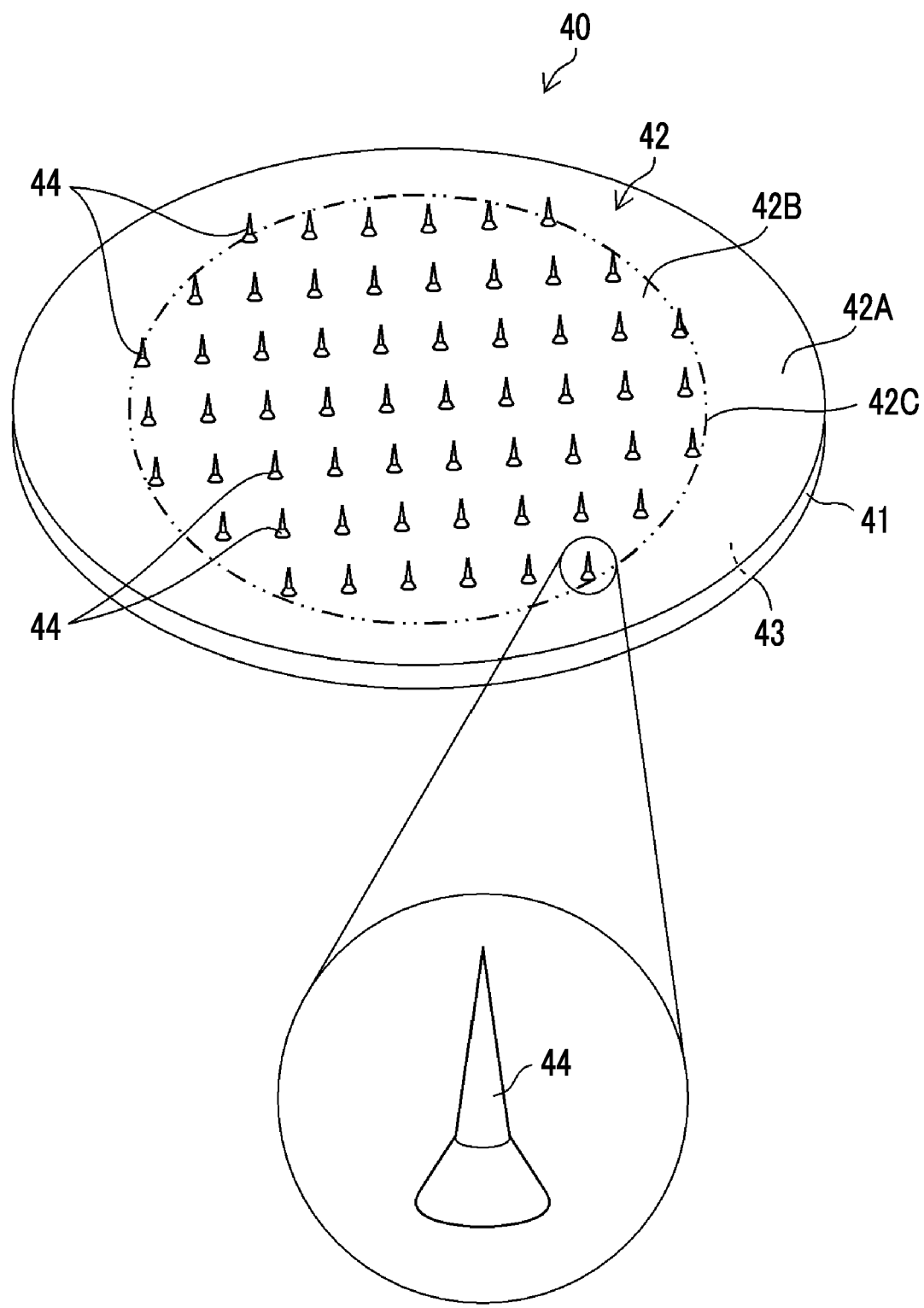
FIG. 1 is a perspective view illustrating a microneedle array.

A typical structure of a microneedle array 40 will be described with reference to FIG. 1. FIG. 1 is a perspective view illustrating a microneedle array 40 for one dose. As illustrated in FIG. 1, the microneedle array 40 comprises a circular sheet 41 having one surface 42 and the other surface 43 which oppose each other and a plurality of needles 44 arranged on the one surface 42 of the sheet 41. The needles 44 constitute microneedles. The plurality of needles 44 are arranged in a microneedle region 42B inside an outer peripheral surface 42A of the one surface 42. As illustrated in FIG. 1, the boundary between the outer peripheral surface 42A and the microneedle region 42B is an imaginary line 42C that connects the needles 44, which are arranged on the outermost side of the microneedle region 42B, from among the plurality of needles 44. According to the embodiment, an example in which the sheet 41 has a circular shape has been described, but the sheet 41 may have a rectangular shape.

The shape and the size of the sheet 41 or the needles 44 may be selected according to the applications of the microneedle array 40. Further, the sheet 41 and the needles 44 may be formed of the same material or different materials. The microneedle array 40 can be produced by integrally forming the sheet 41 and the needles 44, but the sheet 41 and the needles 44 may be formed separately.

The needles 44 respectively have, for example, a substantially cone shape, but may have a columnar shape or a frustum shape. According to the embodiment, the needles 44 are formed in order of a truncated cone portion and a cone from the one surface 42 toward the tip, but the shape thereof is not particularly limited as long as the skin can be punctured by the needles. It is preferable that the needles 44 are arranged in an array in a state of columns (lateral rows) and rows (vertical rows) at equal intervals.

Each needle 44 may be formed of a metal material, but it is preferable that each needle 44 is formed of a material that is dissolved after the skin or the mucous membrane is punctured by the needles so that the needles are inserted into the body. Accordingly, as the material constituting the needles 44, a water-soluble polymer is preferable and polysaccharides are more preferable. As the material constituting the needles 44, it is preferable that the needles are formed of at least one material selected from the group consisting of hydroxyethyl starch, dextran, chondroitin sulfate, sodium hyaluronate, carboxymethyl cellulose, polyvinylpyrrolidone, polyoxyethylene polyoxypropylene glycol, and polyethylene glycol.

Each needle 44 is coated with or contains a drug. Each needle 44 penetrates the skin to puncture the body in a case of attaching the sheet 41 to the surface of the skin. In a case where each needle 44 is coated with the drug, the drug is administered into the body from the surface of each needle 44. Further, in a case where the drug is contained in each needle 44, since each needle 44 is formed of a material that is dissolved after each needle 44 is used to puncture the body, the drug in the needle 44 is administered into the body due to the dissolution of the needle 44 in the body.

The sheet 41 of the microneedle array 40 has a diameter of 10 mm to 30 mm and a thickness of 0.1 mm to 5 mm. Further, each needle 44 has a length of 0.2 mm to 1.5 mm. Further, the number of needles 44 to be arranged on the one surface 42 of the sheet 41 is in a range of 4 to 1000. However, the values are not limited thereto. In the array preparing step, for example, the microneedle array 40 having the above-described structure is prepared.

Figure 2:
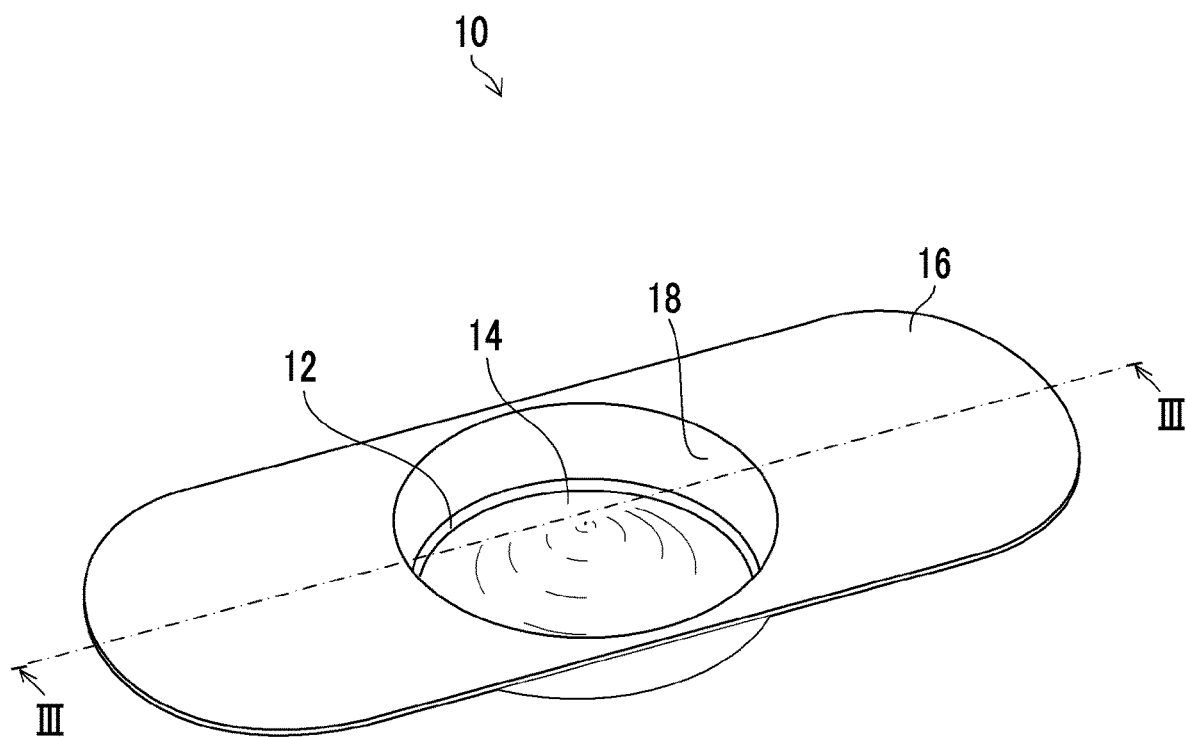
FIG. 2 is a perspective view illustrating a container.
Figure 3:
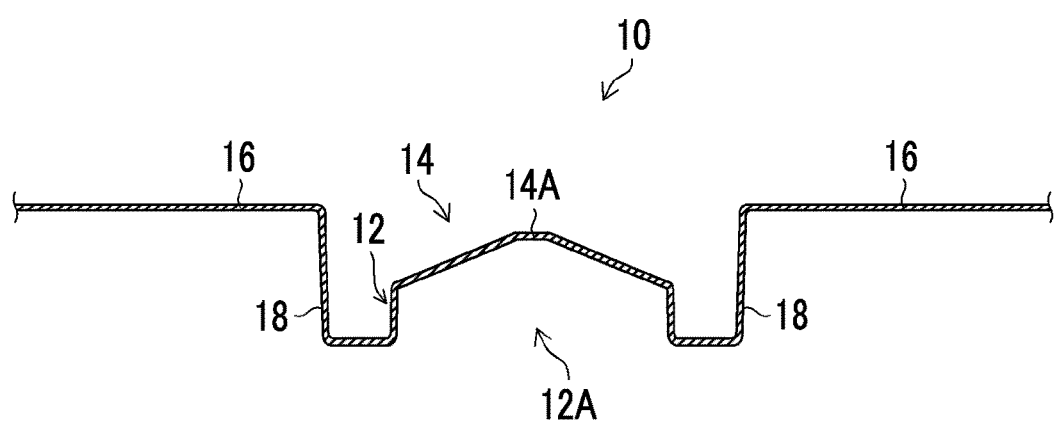
FIG. 3 is a cross-sectional view taken along the line III-III of FIG. 2.

Next, the container 10 will be described. FIG. 2 is a perspective view illustrating the container, and FIG. 3 is a cross-sectional view taken along the line III-III of FIG. 2. The container 10 will be described with reference to FIGS. 2 and 3.

As illustrated in FIG. 2, the container 10 comprises an accommodating portion 12 for accommodating the microneedle array 40, and a deformable portion 14 integrated with the accommodating portion 12. Further, the container 10 comprises a flange portion 16 which is integrated with the accommodating portion 12 and bent by a bent portion 18.

The accommodating portion 12 and the deformable portion 14 of the container 10 respectively have a circular shape in a plan view. The flange portion 16 of the container 10 has a racetrack shape (shape formed by combining two semicircles and two straight lines) in a plan view. However, the shapes of the accommodating portion 12, the deformable portion 14, and the flange portion 16 are not limited. In the embodiment, the flange portion 16 is provided in the entire circumference of the accommodating portion 12. The entire circumference means that the entire circumference of the accommodating portion 12 is enclosed by the flange portion 16. The flange portion 16 is not necessarily provided in the entire circumference of the accommodating portion 12. Further, it is preferable that the flange portion 16 contains an adhesive on the surface to be brought into contact with the skin. The container 10 is attached to the skin because of the adhesive of the flange portion 16. Even in a case where the flange portion 16 does not contain an adhesive, the container 10 is attached to the skin because of an adhesive applied to the skin. Further, the container 10 can be attached to the skin by attaching another member (medical tape) or the like to the container 10.

As illustrated in FIG. 3, the accommodating portion 12 has a space that accommodates the microneedle array 40 and an opening 12A defined by a wall portion. The microneedle array 40 is inserted into the container 10 or discharged from the container 10 through the opening 12A of the accommodating portion 12. The accommodating portion 12 has a cylindrical shape according to the embodiment, but the shape of the accommodating portion 12 is not limited as long as the microneedle array 40 can be accommodated therein.

The deformable portion 14 is disposed on a side opposite to the opening 12A and integrated with the accommodating portion 12. In the embodiment, the deformable portion 14 has, for example, a convex shape having a vertex portion 14A positioned in a direction away from the opening 12A of the accommodating portion 12. The vertex portion 14A of the deformable portion 14 indicates a portion furthest from the opening 12A in the deformable portion 14, and the convex shape indicates that the vertex portion 14A is not positioned in the space of the accommodating portion 12. The deformable portion 14 may have a plurality of vertex portions 14A. The integration indicates that the accommodating portion 12 and the deformable portion 14 are connected with each other. For example, the integration of the accommodating portion 12 with the deformable portion 14 can be realized by integrally forming the accommodating portion 12 and the deformable portion 14. Alternatively, the integration of the accommodating portion 12 with the deformable portion 14 can be also realized by separately forming the accommodating portion 12 and the deformable portion 14, fitting the accommodating portion 12 and the deformable portion 14 to each other, and then welding these. However, the integration method is not limited to these methods.

The deformable portion 14 can be formed in a cone shape. According to the embodiment, the deformable portion 14 has a conical shape. The deformable portion 14 has, for example, a space defined therein. The space of the deformable portion 14 and the space of the accommodating portion 12 can communicate with each other. The accommodating portion 12 has a structure in which the side opposite to the opening 12A is closed by the deformable portion 14. The type of the cone shape includes a conical shape, a pyramid shape, and a frustum shape.

The flange portion 16 is integrated with the accommodating portion 12 and brought into contact with the skin as described below. According to the embodiment, the flange portion 16 extends to the outside from the position of the opening 12A of the accommodating portion 12 and is bent to the side of the deformable portion 14 by the bent portion 18. According to the embodiment, the flange portion 16 is disposed at a position beyond the vertex portion 14A of the deformable portion 14 with respect to the opening 12A of the accommodating portion 12. However, the positional relationship between the flange portion 16 and the deformable portion 14 is not particularly limited. The shape of the flange portion 16 is not particularly limited as long as the flange portion can be brought into contact with the skin. In a case where the accommodating portion 12 is integrated with the flange portion 16, the same method used for integration of the accommodating portion 12 with the deformable portion 14 can be applied. In the container preparing step, for example, the container 10 is prepared.

It is preferable that the container 10 is formed of, for example, a polyethylene resin, a polypropylene resin, or a mixture thereof. However, the materials are not limited thereto. It is preferable that these materials respectively satisfy the "Specification of Plastic Container for Aqueous Injections (hereinafter, simply referred to as an injection container grade)". Further, the container 10 may be formed of various resin materials that satisfy the same specification.

Figure 4:
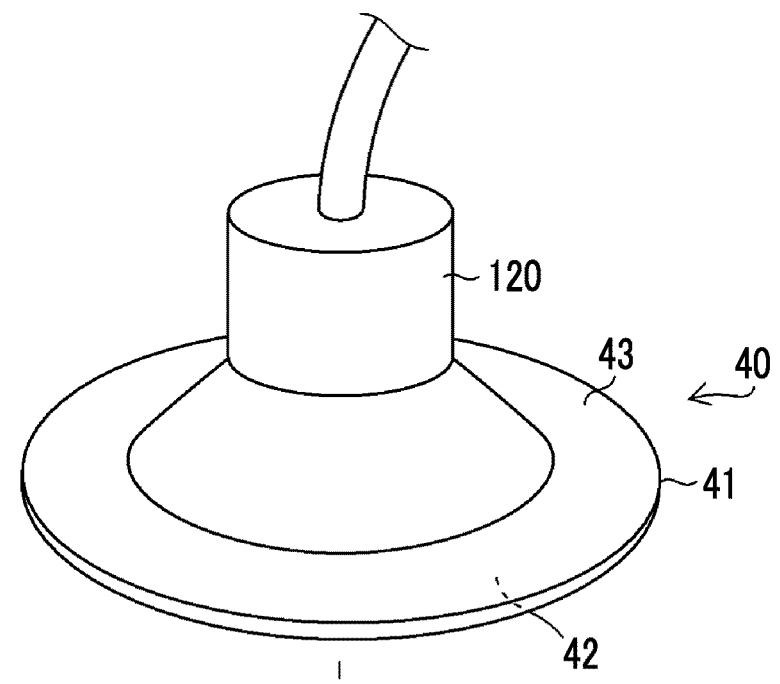
FIG. 4 is a step view illustrating a method of producing a microneedle array unit.
Figure 4:
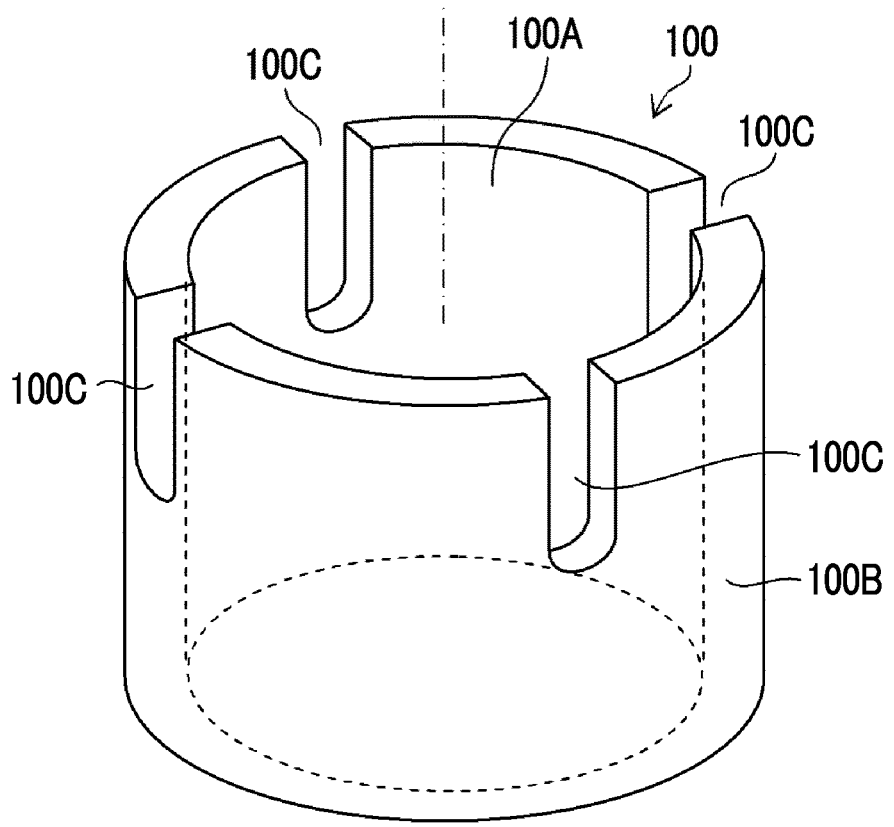

Next, the method of producing the microneedle array unit which includes the accommodating step and the deforming step will be described with reference to FIGS. 4 to 12. As illustrated in FIG. 4, a support 100 that supports the microneedle array 40 is prepared. The support 100 includes a wall portion 100B defining an opening 100A, and has a hollow structure having a space formed inside the wall portion 100B. In the embodiment, the support 100 has a columnar shape as a whole. The shape of the support 100 is not particularly limited as long as the support can support the microneedle array 40.

A notch 100C extending downward from the opening 100A is formed in the wall portion 100B of the support 100. The notch 100C is open on a side of the opening 100A and closed on the other side, and further penetrates the wall portion 100B. The support 100 is provided in a state where the opening 100A faces upward.

The other surface 43 of the sheet 41 of the microneedle array 40 is adsorbed by an adsorption pad 120 from above the sheet 41. The needles 44 of the microneedle array 40 face downward and are arranged to oppose the opening 100A of the support 100. Since the adsorption pad 120 adsorbs the other surface 43 of the sheet 41, the microneedle array 40 can be transported without damaging the needles 44.

Figure 5:
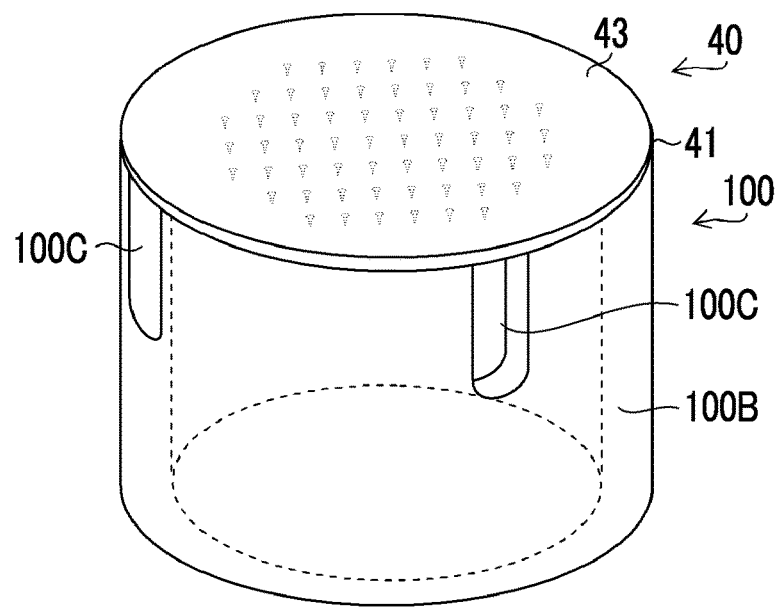
FIG. 5 is a step view illustrating the method of producing a microneedle array unit.

Next, as illustrated in FIG. 5, the microneedle array 40 is placed on the support 100. The one surface 42 of the sheet 41 is brought into contact with an upper portion of the wall portion 100B, and the one surface 42 of the sheet 41 of the microneedle array 40 is supported by the support 100 from below. Since the needles 44 of the microneedle array 40 are positioned in the opening 100A (not illustrated) and the support 100 has a hollow structure, the support 100 supports the one surface 42 of the sheet 41 in a non-contact manner with the needles 44 of the microneedle array 40.

By connecting a suction device (not illustrated) to the support 100, the one surface 42 of the sheet 41 of the microneedle array 40 can be sucked downward from the opening 100A. The support 100 can stably support the microneedle array 40 by allowing the suction device to suck the one surface.

Figure 6:
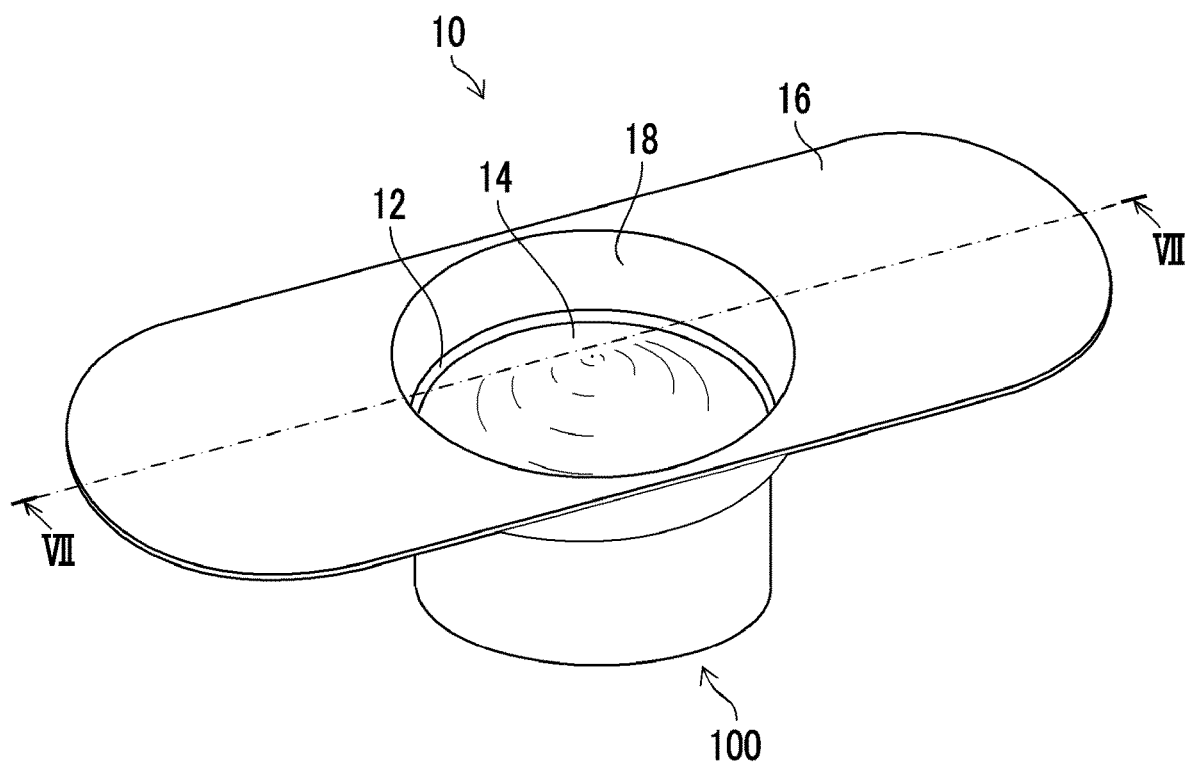
FIG. 6 is step view illustrating the method of producing a microneedle array unit.
Figure 7:
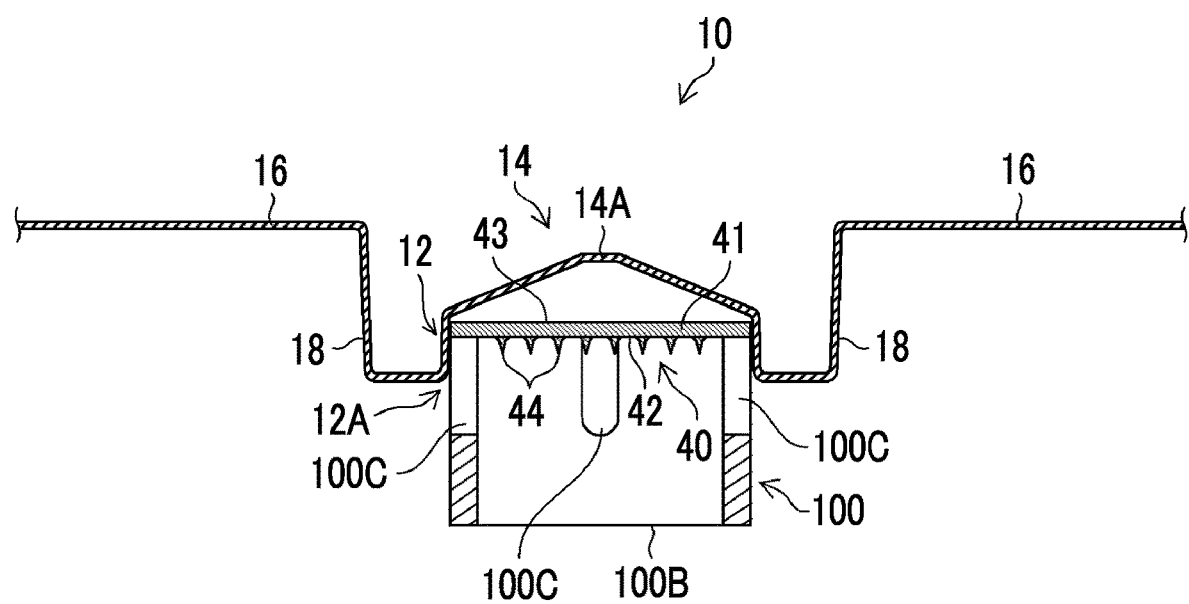
FIG. 7 is a cross-sectional view taken along the line VII-VII of FIG. 6.

Next, as illustrated in FIGS. 6 and 7, the opening 12A (not illustrated) of the accommodating portion 12 is directed downward. The other surface 43 of the sheet 41 of the microneedle array 40 and the deformable portion 14 of the container 10 are disposed to oppose each other. The microneedle array 40 is accommodated in the accommodating portion 12 of the container 10. The opening 12A of the accommodating portion 12 is larger than the outer shape of the support 100. Therefore, a part of the support 100 including the notch 100C is accommodated in the accommodating portion 12 of the container 10.

Figure 8:
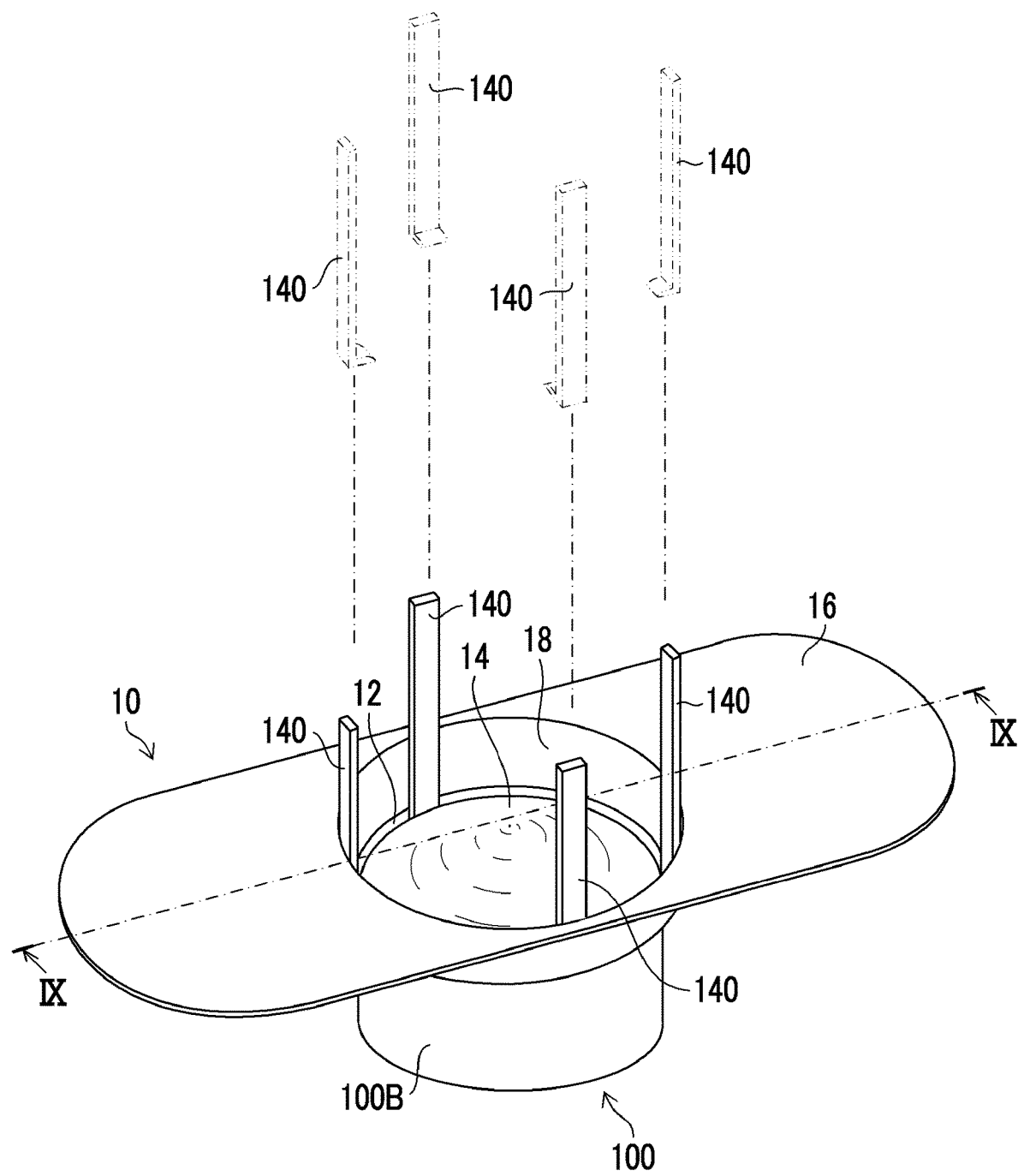
FIG. 8 is a step view illustrating the method of producing a microneedle array unit.
Figure 9:
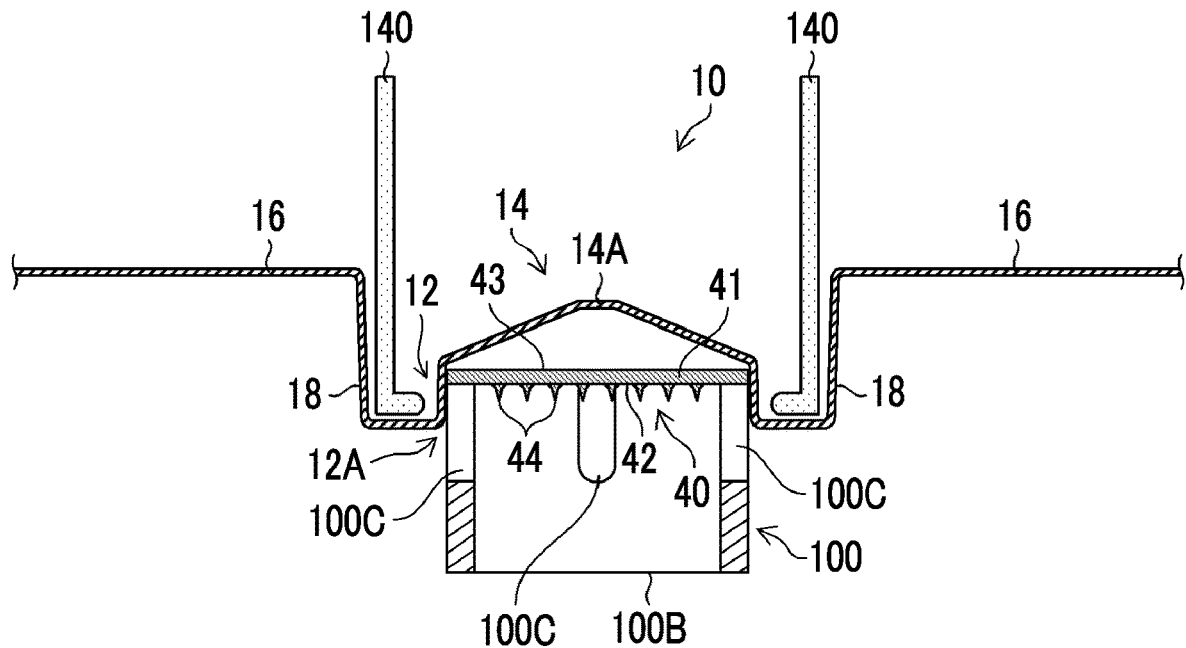
FIG. 9 is a cross-sectional view taken along the line IX-IX of FIG. 8.

Next, as illustrated in FIGS. 8 and 9, a pressing jig 140 is prepared. The pressing jig 140 is used to deform the outer surface of the accommodating portion 12 of the container 10 inward. The pressing jig 140 is prepared according to the sites of the accommodating portion 12 intended to be deformed and the number of sites. The pressing jig 140 includes a rod-like member extending in the vertical direction and a protruding portion formed on the lower side of the member. The pressing jig 140 moves to a position between the accommodating portion 12 and the bent portion 18, which corresponds to the notch 100C of the support tool 100.

Figure 10:
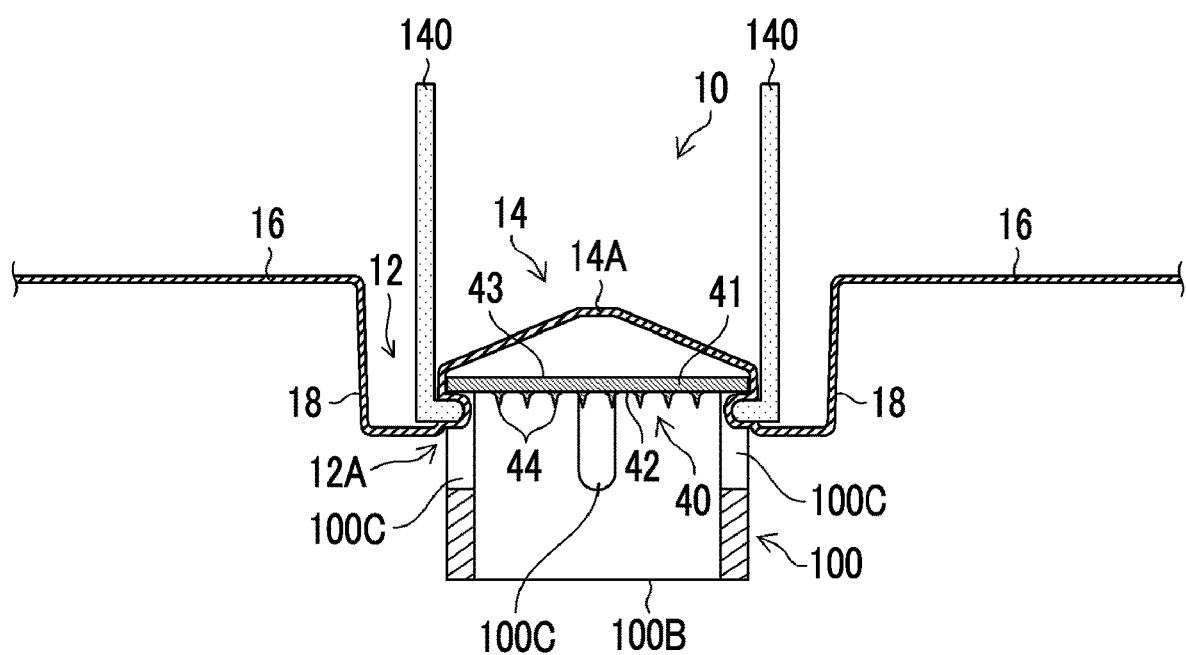
FIG. 10 is a step view illustrating the method of producing a microneedle array unit.

Next, as illustrated in FIG. 10, the pressing jig 140 is pressed against the outer surface of the accommodating portion 12 toward the notch 100C of the support 100. The protruding portion of the pressing jig 140 deforms the outer surface of the accommodating portion 12 inward toward the notch 100C. The outer surface of the accommodating portion 12 positioned between the opening 12A and the one surface 42 of the sheet 41 of the microneedle array 40 is deformed inward. The wall portion 100B is disposed in a portion of the accommodating portion 12 which is not intended to be deformed, and the notch 100C is disposed in a portion of the accommodating portion 12 which is intended to be deformed. Therefore, the outer surface of the accommodating portion 12 can be locally deformed by allowing the protruding portion of the pressing jig 140 to move toward the notch 100C. It is preferable that the pressing jig 140 is heated with a heater (not illustrated) or the like. The outer surface of the accommodating portion 12 of the container 10 can be easily deformed by heating the pressing jig 140.

Figure 11:
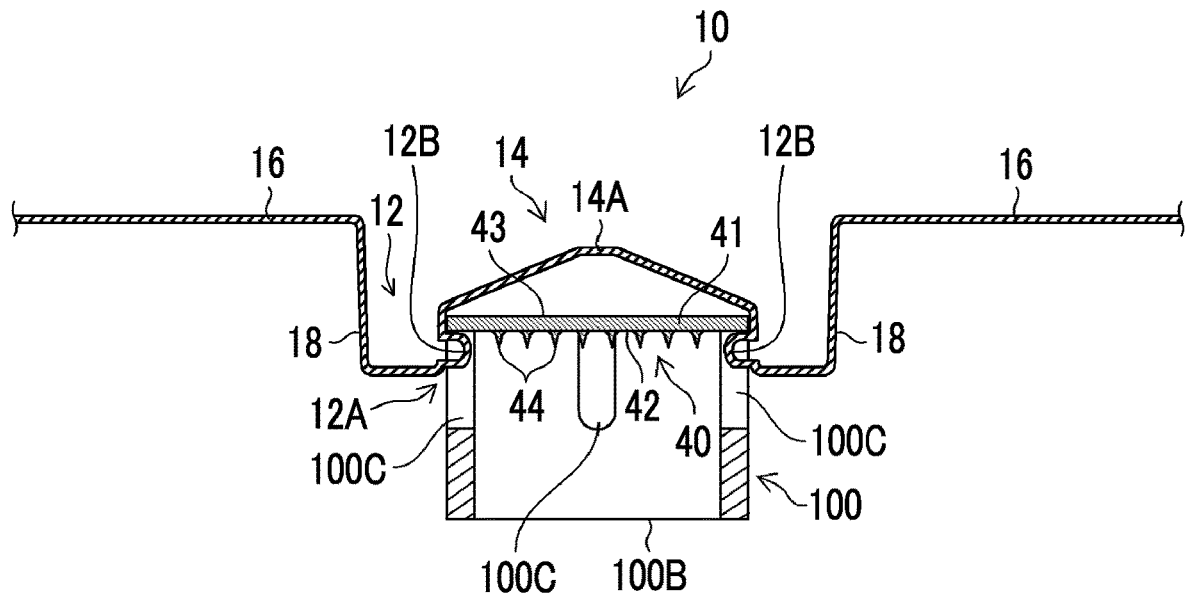
FIG. 11 is a step view illustrating the method of producing a microneedle array unit.

Next, the pressing jig 140 is retracted in a direction away from the accommodating portion 12 and allowed to move upward. As illustrated in FIG. 11, protrusions 12B that protrude to the space of the accommodating portion 12 are formed on the inner surface of the accommodating portion 12. As illustrated in FIG. 11, the protrusions 12B enter the notch 100C and extend to the space of the support 100 in a cross-sectional view. A microneedle array unit 1 in a first form in which the microneedle array 40 is accommodated in the container 10 is produced.

Figure 12:
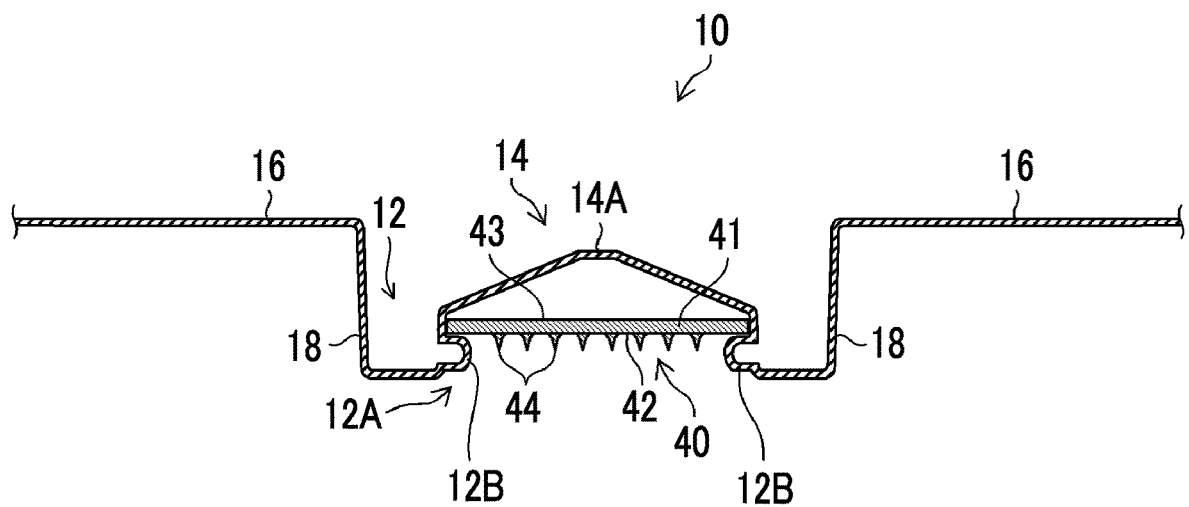
FIG. 12 is a step view illustrating the method of producing a microneedle array unit.
Figure 12:
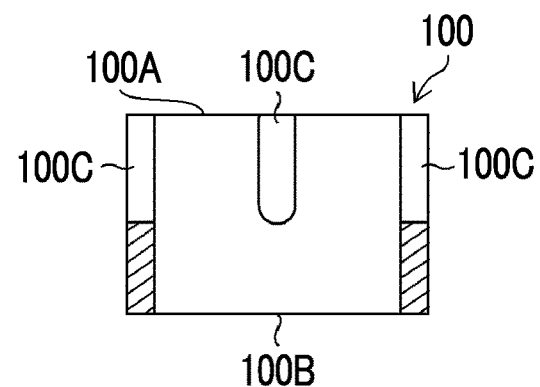

Next, as illustrated in FIG. 12, the microneedle array unit 1 comprising the container 10 and the microneedle array 40 accommodated in the container 10 is taken out from the support 100. The microneedle array unit 1 is allowed to move upward with respect to the support 100 using a transport device (not illustrated) or the like. The protrusions 12B of the accommodating portion 12 enter the notch 100C of the support 100. In addition, since the side of the opening 100A of the notch 100C is open, the protrusions 12B of the accommodating portion 12 can be allowed to move upward along the notch 100C to a position separated from the support 100. Therefore, the microneedle array unit 1 can be easily taken out from the support 100.

As illustrated in FIG. 12, in a state in which the tips of the plurality of needles 44 are directed downward, the protrusions 12B support a portion of the one surface 42 of the microneedle array 40, which is a region (the outer peripheral surface 42A in FIG. 1) where the needles 44 are not formed. In a state in which the opening 12A of the container 10 is directed downward, falling of the microneedle array 40 from the space of the accommodating portion 12 is prevented by the protrusions 12B, and the microneedle array 40 is accommodated in the container 10.

The other surface 43 of the microneedle array 40 opposes the deformable portion 14. According to the embodiment, the deformable portion 14 has a conical shape and the inner diameter of the deformable portion 14 decreases toward the vertex portion 14A. Even in a case where the container 10 is vibrated during the transport or the like, movement of the microneedle array 40 is restricted by the protrusions 12B and the deformable portion 14. In the microneedle array unit 1 according to the embodiment, an adhesive for holding the microneedle array 40 is not disposed. Therefore, the accommodating step and the deforming step can be performed in a sterile environment. As an example of the sterile environment, a grade A environment in terms of air cleanliness in a pharmaceutical production facility can be exemplified. The grade A in which the cleanliness level is defined by EU Guidelines to Good Manufacturing Practice Medical Products for Human and Veterinary Use (EU-GMP) indicates that "the number of the maximum allowable particles each having a particle diameter of 0.5 μm or greater which are contained in 1 m$^3$ of air in a case of working and non-working is 3520 or less".

Figure 13:
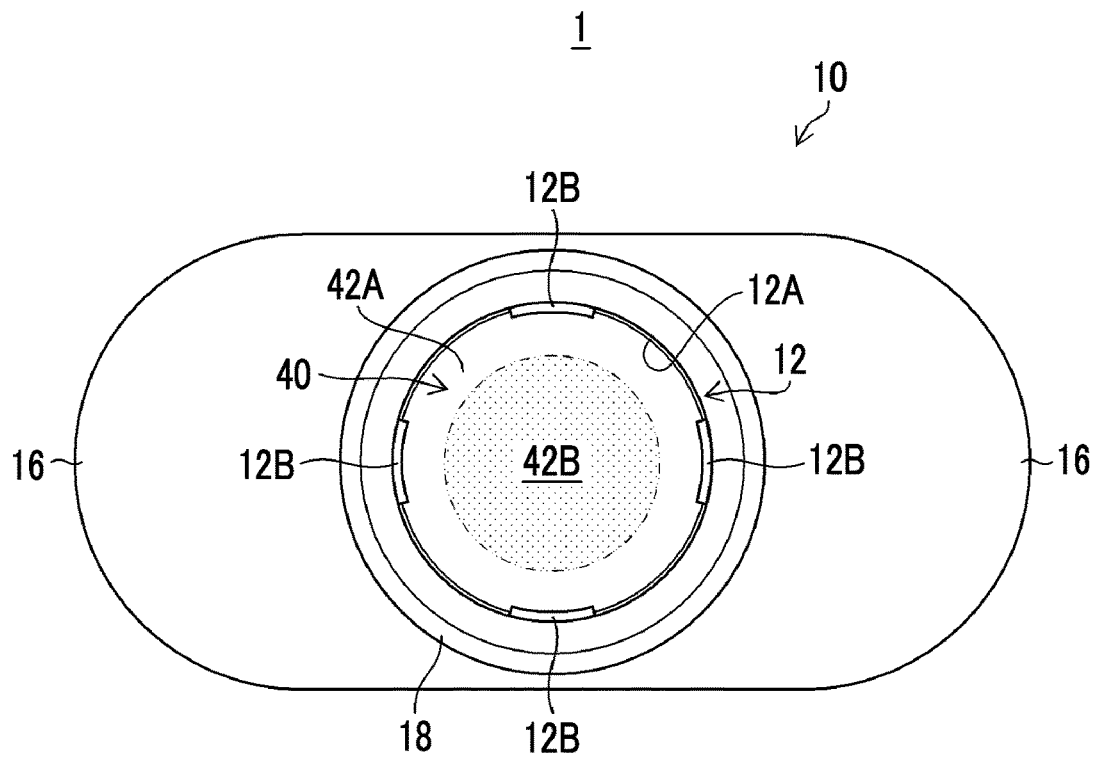
FIG. 13 is a view illustrating the microneedle array unit as seen from an opening of the container.

FIG. 13 is a view illustrating the microneedle array unit 1 as seen from the opening 12A of the accommodating portion 12 of the container 10. As illustrated in FIG. 13, four protrusions 12B are provided in the wall portion of the accommodating portion 12 at equal intervals. Four protrusions 12B support the outer peripheral surface 42A of the microneedle array 40. The protrusions 12B of the accommodating portion 12 reduce the area of the opening 12A of the accommodating portion 12. By comparing the projected area of the opening 12A before the formation of the protrusions 12B and the projected area of the opening 12A after the formation of the protrusions 12B, it is determined whether the area of the opening 12A is reduced by the protrusions 12B. Since the area of the opening 12A is reduced by the protrusions 12B, it is possible to suppress falling of the microneedle array 40 from the container 10.

In the embodiment, the case where four protrusions 12B are formed in the accommodating portion 12 has been described, but the size, the shape, and the number of the protrusions 12B are not limited as long as falling of the microneedle array 40 from the container 10 can be suppressed. It is preferable that at least two protrusions 12B are formed. The microneedle array 40 can be stably accommodated in the container.

In the embodiment, since the protrusions 12B are formed in the accommodating portion 12 of the container 10 after the microneedle array 40 is accommodated in the container 10, the microneedle array 40 can be accommodated and held in the container 10 without applying a load to the microneedle array 40.

It is preferable that the method of producing the microneedle array unit 1 comprises a sealing step. The microneedle array 40 can be protected from contamination until the skin is punctured by sealing the microneedle array unit 1.

Figure 14:
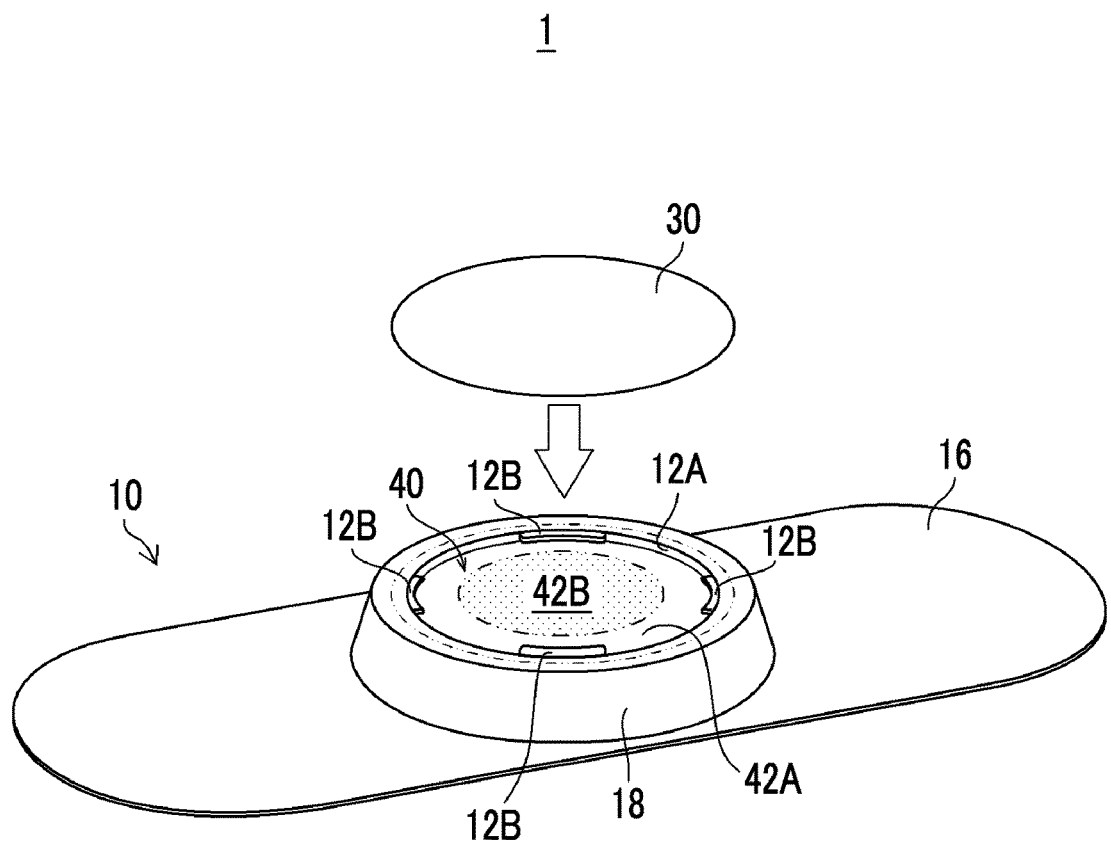
FIG. 14 is a step view illustrating a sealing step for the microneedle array unit.

As illustrated in FIG. 14, the microneedle array unit 1 is sealed by sealing the opening 12A of the accommodating portion 12 with the lid 30 in the sealing step. The space for accommodating the microneedle array 40 is sealed by the lid 30 and the container 10 so that entrance of foreign matter can be prevented.

Figure 15:
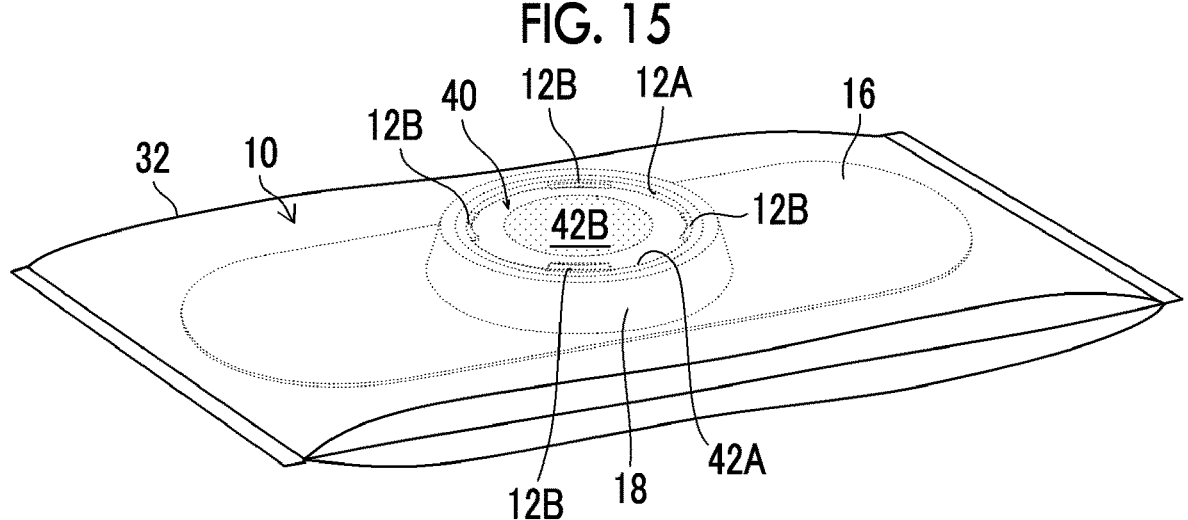
FIG. 15 is a step view illustrating another sealing step for the microneedle array unit.

As illustrated in FIG. 15, the microneedle array unit 1 is sealed by putting the microneedle array unit 1 in the bag 32 and sealing the bag 32. The space for accommodating the microneedle array 40 is sealed by the bag 32 so that entrance of foreign matter can be prevented.

It is preferable that the lid 30 and the bag 32 are formed of, for example, a polyethylene resin, a polypropylene resin, or a mixture thereof. However, the materials are not limited thereto. It is preferable that these materials respectively satisfy the "Specification of Plastic Container for Aqueous Injections (hereinafter, simply referred to as an injection container grade)". Further, the lid 30 and the bag 32 may be formed of various resin materials satisfying the same specification other than those described above.

Figure 16:
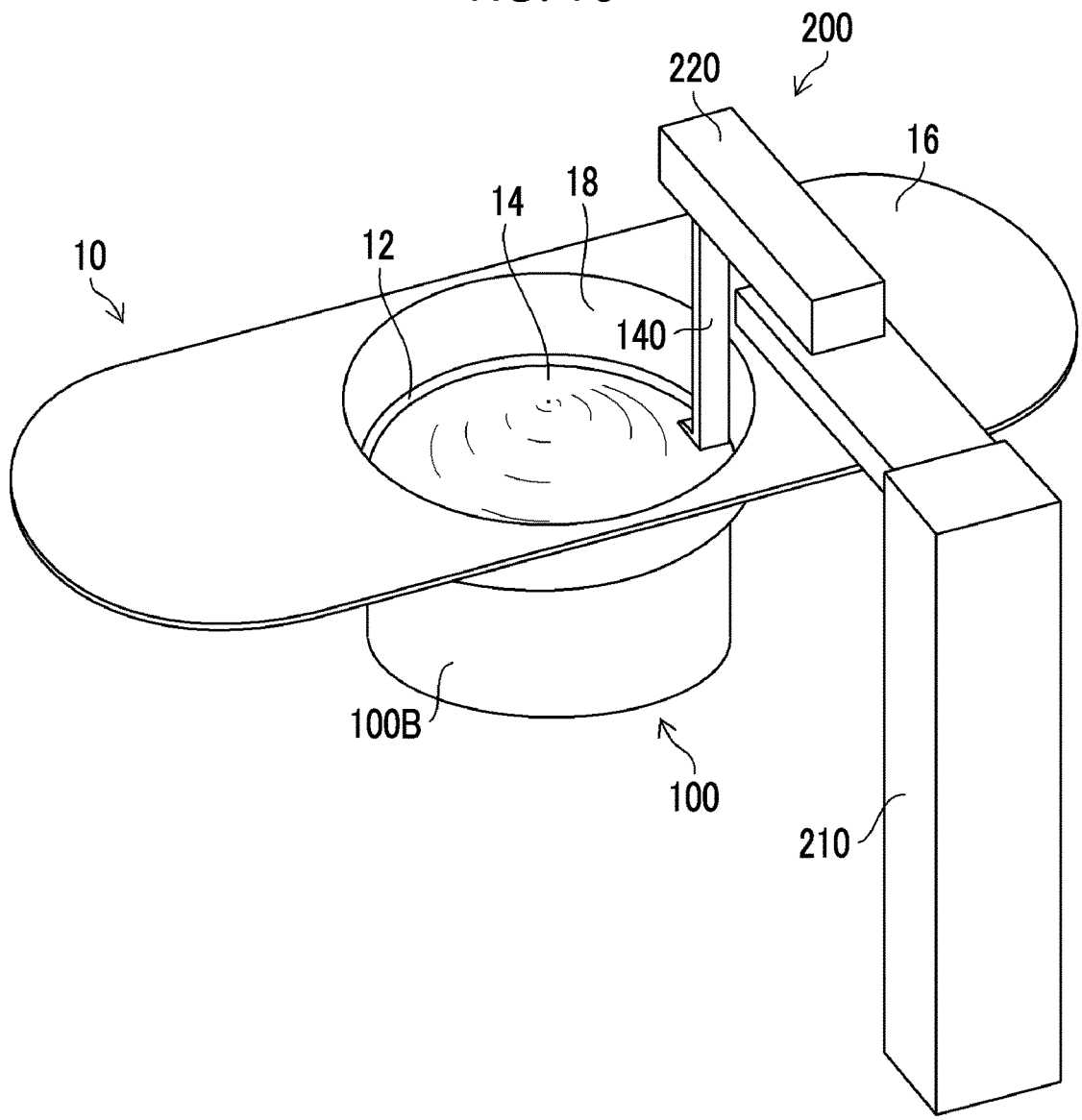
FIG. 16 is a schematic configuration view illustrating a driving device.

FIG. 16 describes a driving device for driving the operation of the pressing jig 140. A driving device 200 comprises a Z-axis driving mechanism 210 that drives the pressing jig 140 in the vertical direction, and an X-Y axis driving mechanism 220 that is connected to the Z-axis driving mechanism 210 and drives the pressing jig 140 in the horizontal direction. A control device (not illustrated) is connected to the driving device 200, and the control device controls the Z-axis driving mechanism 210 and the X-Y axis driving mechanism 220. The driving device 200 controls the operation of the pressing jig 140. For example, the time and the pressing force for pressing the outer surface of the accommodating portion 12 are controlled. Further, FIG. 16 illustrates only the driving device 200 that drives one pressing jig 140. The driving device 200 may be prepared according to the number of the protrusions 12B. A plurality of protrusions 12B can be formed simultaneously. In addition, a plurality of protrusions 12B may be sequentially formed by preparing the driving device 200 that drives one pressing jig 140 and allowing the pressing jig 140 to move to a portion where the protrusion 12B is intended to be formed.

Next, the step of puncturing the skin with the microneedle array 40 using the microneedle array unit 1 will be described with reference to FIGS. 17 to 20.

Figure 17:
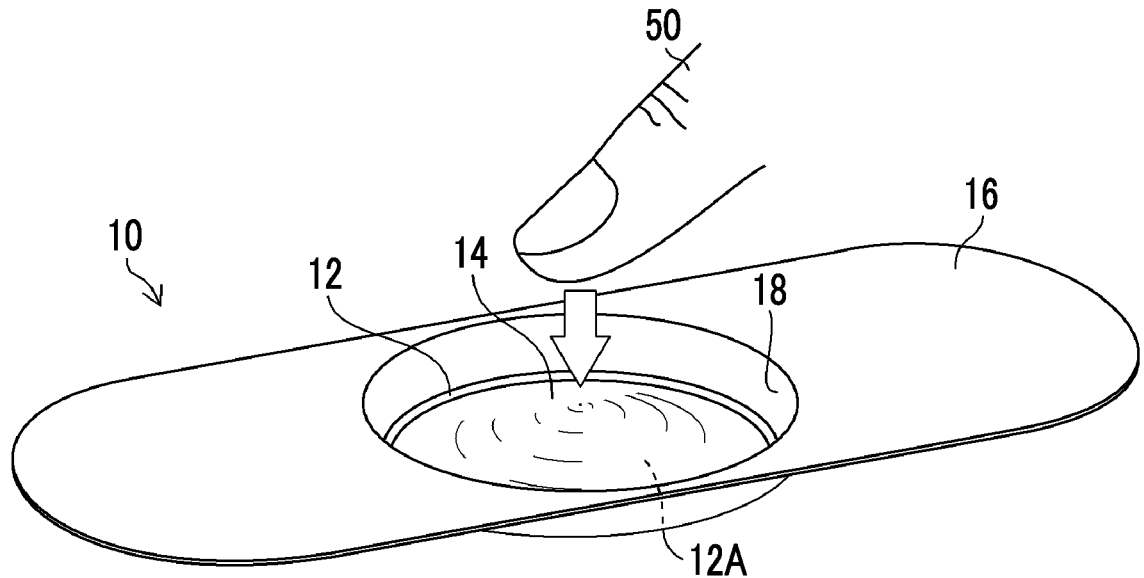
FIG. 17 is a perspective view of the microneedle array unit illustrating a step of puncturing the skin with the microneedle array.
Figure 18:
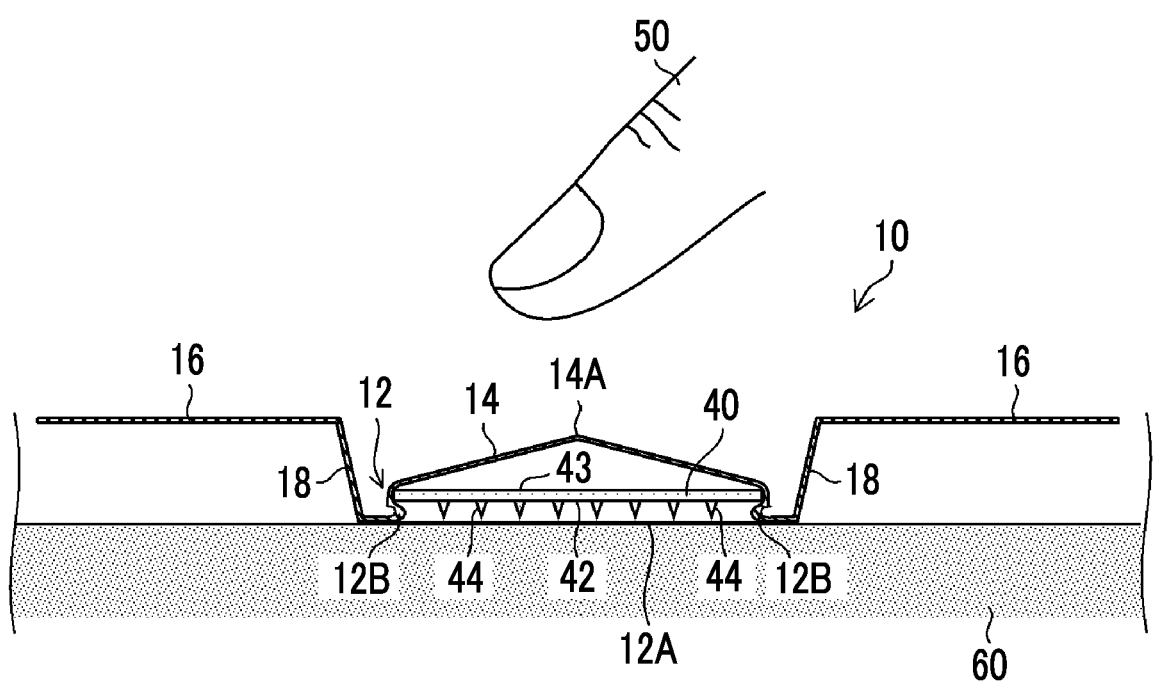
FIG. 18 is a cross-sectional view of the microneedle array unit illustrating the step of puncturing the skin with the microneedle array.
Figure 19:
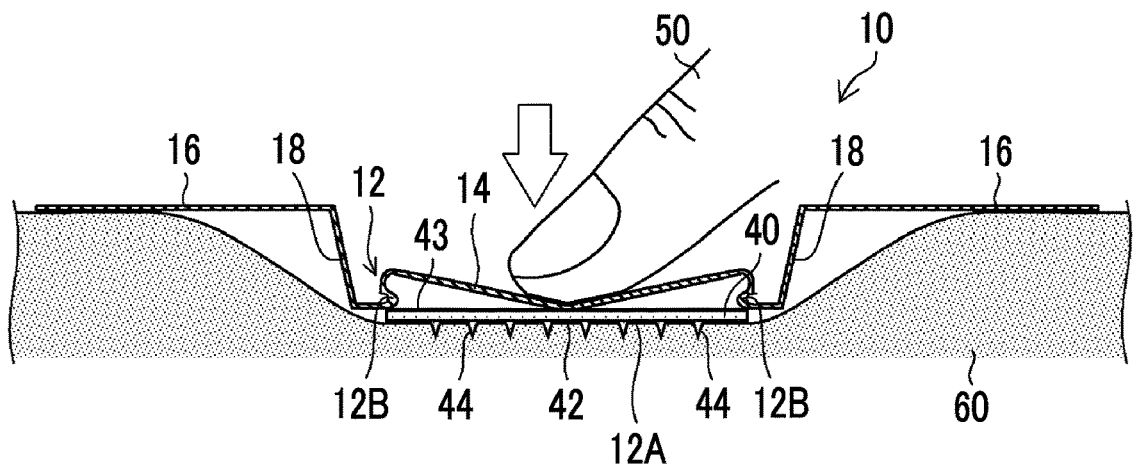
FIG. 19 is a cross-sectional view of the microneedle array unit illustrating the step of puncturing the skin with the microneedle array.
Figure 20:
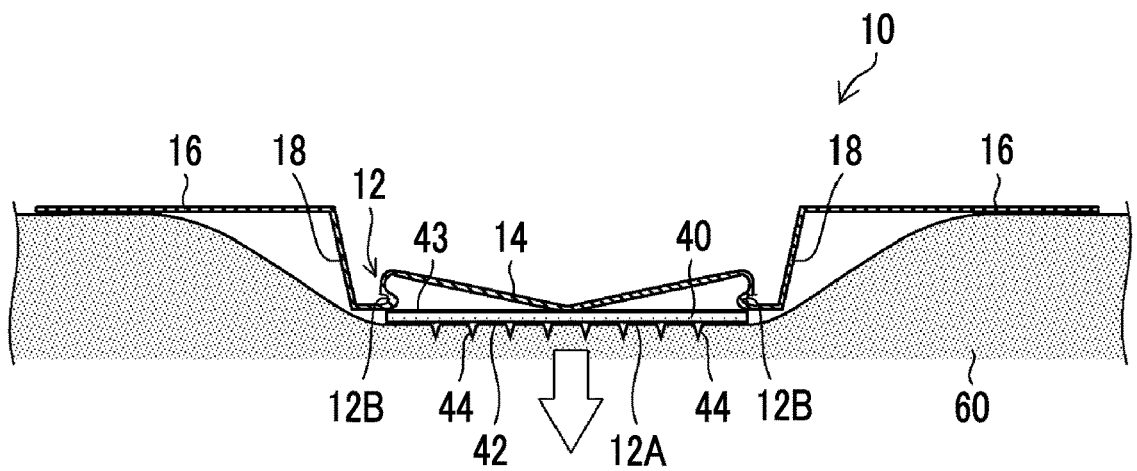
FIG. 20 is a cross-sectional view of the microneedle array unit illustrating the step of puncturing the skin with the microneedle array.

FIG. 17 is a perspective view illustrating the step of puncturing the skin with the microneedle array 40, and FIGS. 18 to 20 are cross-sectional views illustrating the step of puncturing the skin with the microneedle array 40.

In a case where the skin is punctured and the microneedle array unit 1 is sealed, for example, the lid 30 is peeled off from the container 10 or the microneedle array unit 1 is taken out from the bag 32. The microneedle region 42B of the microneedle array 40 is exposed from the opening 12A (see FIG. 13). The microneedle array 40 is protected by the lid 30 or the bag 32 until the microneedle array unit 1 is used.

As illustrated in FIG. 17, the container 10 is positioned on the skin. The opening 12A of the accommodating portion 12 is positioned toward the skin so that the needles 44 (not illustrated) of the microneedle array 40 are directed to the skin. An external force in a direction of the opening 12A is applied to the deformable portion 14 using a finger 50.

FIG. 18 is a cross-sectional view of FIG. 17. As illustrated in FIG. 18, the container 10 is positioned on the skin 60. A portion of the flange portion 16 protruding to the outside from the accommodating portion 12 is brought into contact with the skin 60. The finger 50 is positioned at a position separated from the vertex portion 14A of the deformable portion 14 in order to apply the external force in the direction of the opening 12A to the deformable portion 14. The microneedle array 40 is supported by the protrusions 12B and positioned in the space of the accommodating portion 12.

As illustrated in FIG. 19, the deformable portion 14 is pressed toward the skin 60 using the finger 50. The deformable portion 14 is deformed by receiving the external force in the direction of the opening 12A. The deformable portion 14 presses the other surface 43 of the microneedle array 40. By pressing the other surface 43, the microneedle array 40 passes through the protrusions 12B and is discharged from the accommodating portion 12 to the outside. The microneedle array 40 passes through the opening 12A and the skin 60 is punctured by the needles 44 of the microneedle array 40. It is preferable that the protrusions 12B are elastically deformed in a case of the passage of the microneedle array 40. The elastically deformable protrusions 12B facilitate the discharge of the microneedle array 40 from the accommodating portion 12.

Along with the application of the external force to the deformable portion 14, the skin 60 is moved until the skin comes into contact with the flange portion 16. In a case where the surface of the flange portion 16 which opposes the skin 60 is provided with an adhesive, the flange portion 16 is attached to the skin 60.

As illustrated in FIG. 20, the deformable portion 14 is deformed by the external force. Even after the external force is removed, the deformable portion 14 maintains the deformed shape. The deformed deformable portion 14 presses the microneedle array 40 toward the skin 60.

Since the deformable portion 14 of the container 10 presses the microneedle array 40 until the drug of the microneedle array 40 is administered after the puncture, detachment of the microneedle array 40 from the skin 60 is prevented without the pressing of the finger 50.

According to the embodiment, since the flange portion 16 includes the bent portion 18, a step is formed between the puncture position of the microneedle array 40 and the flange portion 16. Because of the step of the bent portion 18, the microneedle array 40 is pushed down further than the skin 60 that comes into contact with the flange portion 16. By pushing the microneedle array 40 down, a force of the skin 60 to return is increased so that a mutual pressing force between the skin 60 and the microneedle array 40 is increased. Further, the needles 44 of the microneedle array 40 enter a state of easily puncturing the skin 60. It is preferable that the deformed deformable portion 14 is not deformed even in a case of receiving a pressure from the skin 60. The deformable portion 14 is capable of continuously pressing the microneedle array 40.

According to the embodiment, the deformable portion 14 of the container 10 is disposed inside the projection surface of the accommodating portion 12, which accommodates the microneedle array 40, in the vertical direction. Therefore, the disposition of the accommodating portion 12 and the deformable portion 14 in the container 10 leads to a decrease in size of the container 10. As the result, the size of the microneedle array unit 1 is decreased. Consequently, the skin 60 is easily punctured by the microneedle array 40.

A material that enables deformation of the shape of the deformable portion 14 and maintenance of the deformed shape in a case where the deformable portion 14 receives the external force is selected. The material to be used is determined in consideration of the shape and the thickness of the deformable portion 14 and the magnitude of the external force required for the deformation.

Further, as illustrated in FIG. 18, it is preferable that the protrusions 12B are arranged closer to the side of the opening 12A than the side of the deformable portion 14. This means that, in a case where the distance from the opening 12A to the protrusion 12B in the vertical direction and the distance from the position where the deformable portion 14 intersects with the accommodating portion 12 to the protrusion 12B in the vertical direction are compared with each other, the distance from the opening 12A to the protrusion 12B is shorter than the other distance. Here, the vertical direction is based on a case where the opening 12A is provided on the lower side.

In a case where the protrusions 12B are provided on the side of the opening 12A, the needles 44 of the microneedle array 40 are close to the skin 60. In a case where the microneedle array 40 passes through the protrusions 12B and is pushed out from the accommodating portion 12, the skin 60 is immediately punctured by the needles 44, and thus the skin 60 can be stably punctured by the microneedle array 40.

Figure 21:
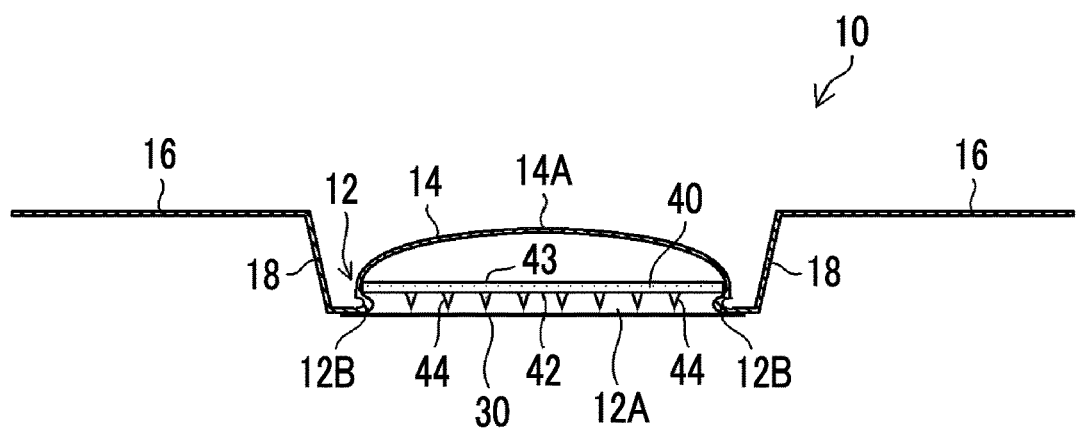
FIG. 21 is a cross-sectional view illustrating a microneedle array unit in a second form.

FIG. 21 is a cross-sectional view illustrating a microneedle array unit 2 in a second form. The configurations which are the same as those of the microneedle array unit 1 are denoted by the same reference numerals, and the description thereof will not be provided.

A difference between the microneedle array unit 2 and the microneedle array unit 1 is the shape of the deformable portion 14.

In the microneedle array unit 2, the deformable portion 14 has a convex shape with the vertex portion 14A and has a dome shape. The dome shape indicates a shape having a curved surface with a certain curvature radius and examples thereof include a hemispherical shape. However, the example is not limited to the hemispherical shape and the curvature radii are not necessarily the same in the entirety of the shape.

The microneedle array unit 2 which includes the deformable portion 14 in the dome shape can be produced by performing the same steps as those for the microneedle array unit 1.

Figure 22:
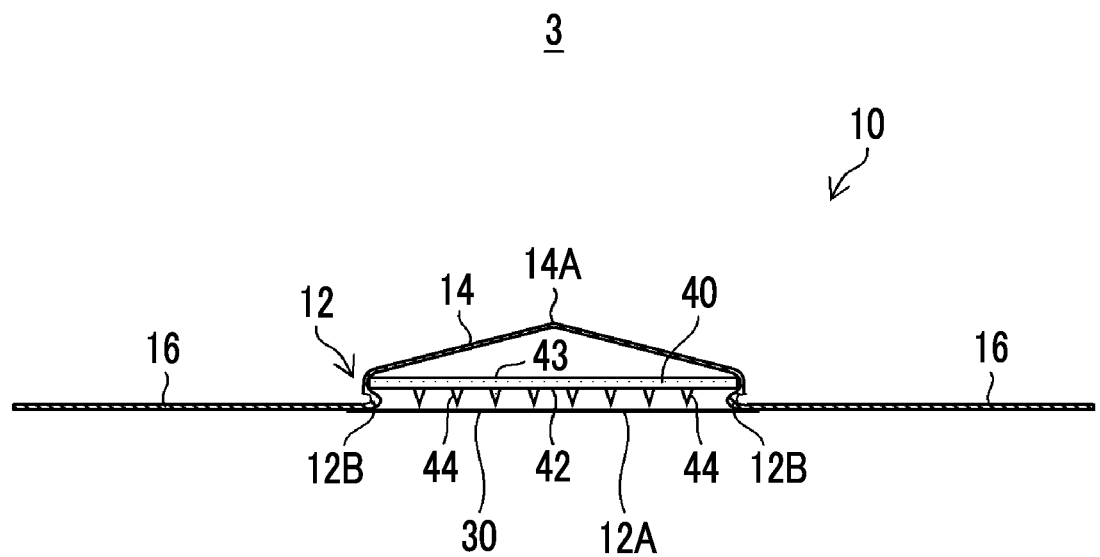
FIG. 22 is a cross-sectional view illustrating a microneedle array unit in a third form.

FIG. 22 is a cross-sectional view illustrating a microneedle array unit 3 in another form. As illustrated in FIG. 22, a difference between the microneedle array unit 3 and the microneedle array unit 1 is the shape of the flange portion 16. In the container 10 of the microneedle array unit 3, the flange portion 16 does not include a bent portion. The flange portion 16 extends to the outside from the position of the opening 12A of the accommodating portion 12. The flange portion 16 is formed to be parallel to the sheet of the microneedle array 40. The concept of parallel includes parallel and substantially parallel. The microneedle array unit 3 is capable of further reducing the pressure between the microneedle array 40 and the skin as compared to the microneedle array unit 1 having a bent portion.

The microneedle array unit 3 having a different shape of the flange portion 16 can also be produced by performing the same steps as those for the microneedle array unit 1.

Figure 23:
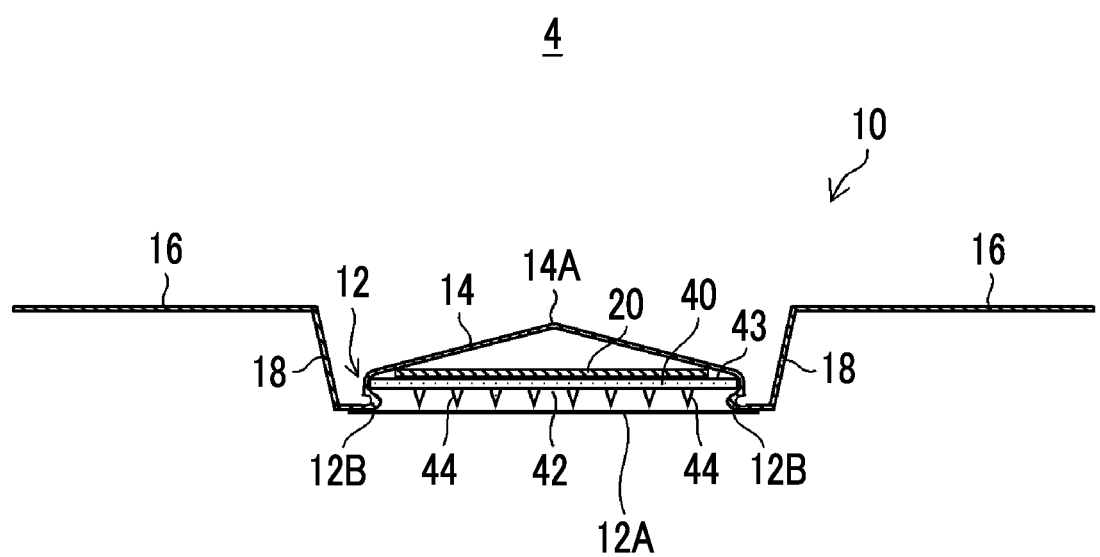
FIG. 23 is a cross-sectional view illustrating a microneedle array unit in a fourth form.

FIG. 23 is a cross-sectional view illustrating a microneedle array unit 4 in still another form. As illustrated in FIG. 23, the microneedle array unit 4 is different from the microneedle array unit 1 in terms that the microneedle array unit 4 comprises a flat plate 20 on a side of the other surface 43 of the microneedle array 40. The flat plate 20 and the container 10 may be separate members or the flat plate 20 may be integrated with the container 10.

The deformable portion 14 is deformed due to the external force and the deformed deformable portion 14 presses the microneedle array 40 into the skin (not illustrated) through the flat plate 20. The entire surface of the microneedle array 40 can be uniformly pressed by the flat plate 20. The microneedle array unit 4 can also be produced by performing the same steps as those for the microneedle array unit 1. The accommodating portion can be accommodated in the container 10 in a state in which the flat plate 20 is placed on the other surface 43 of the microneedle array 40, and the protrusions 12B can be formed in the accommodating portion 12 of the container 10.

Figure 24:
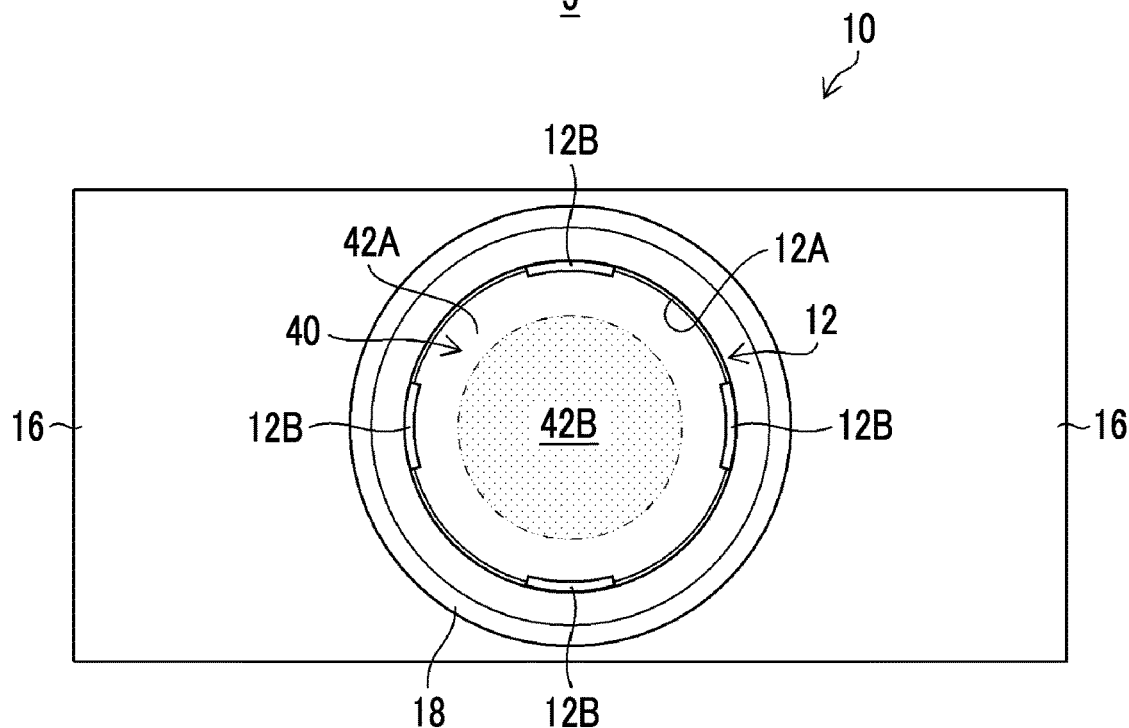
FIG. 24 is a view illustrating microneedle array units in fifth and sixth forms as seen from the opening of the container.
Figure 24:
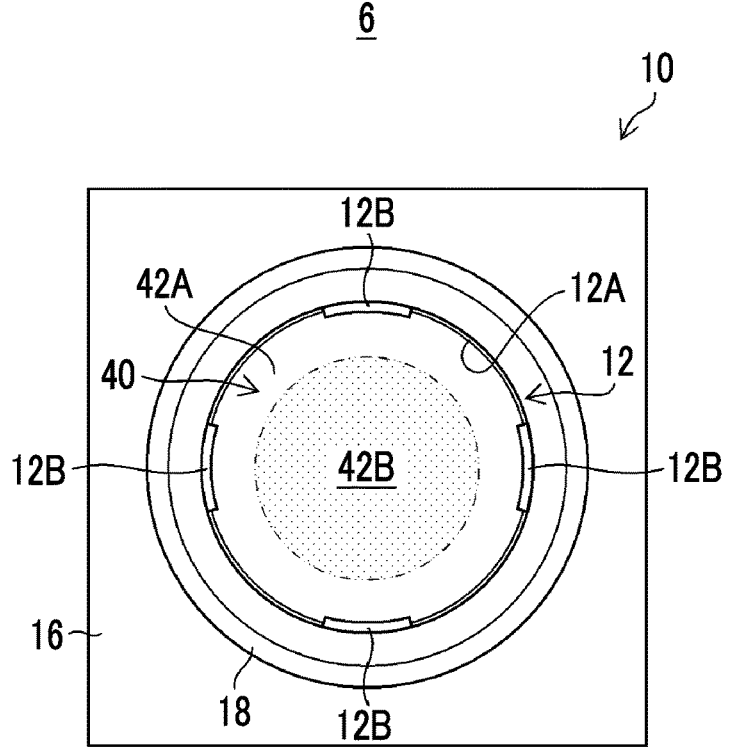
Figure 25:
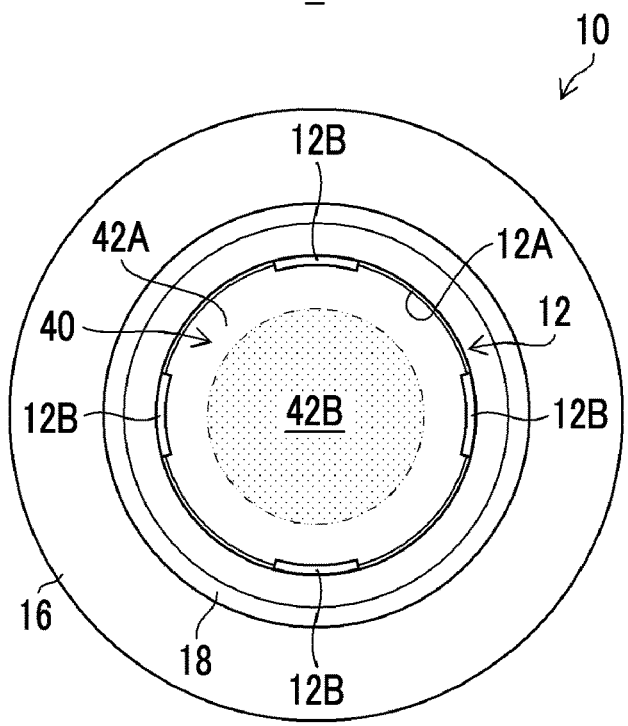
FIG. 25 is a view illustrating microneedle array units in seventh and eighth forms as seen from the opening of the container.
Figure 25:
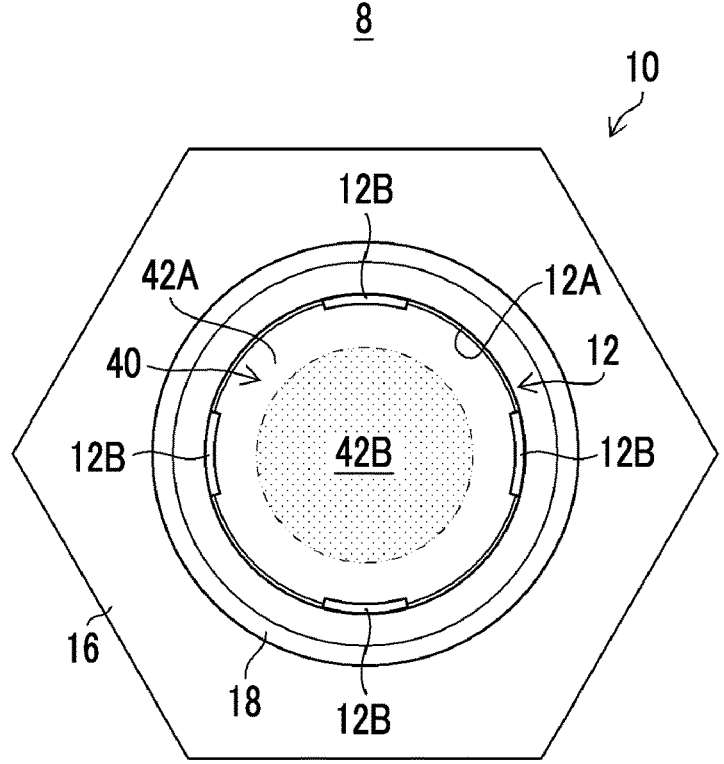
Figure 26:
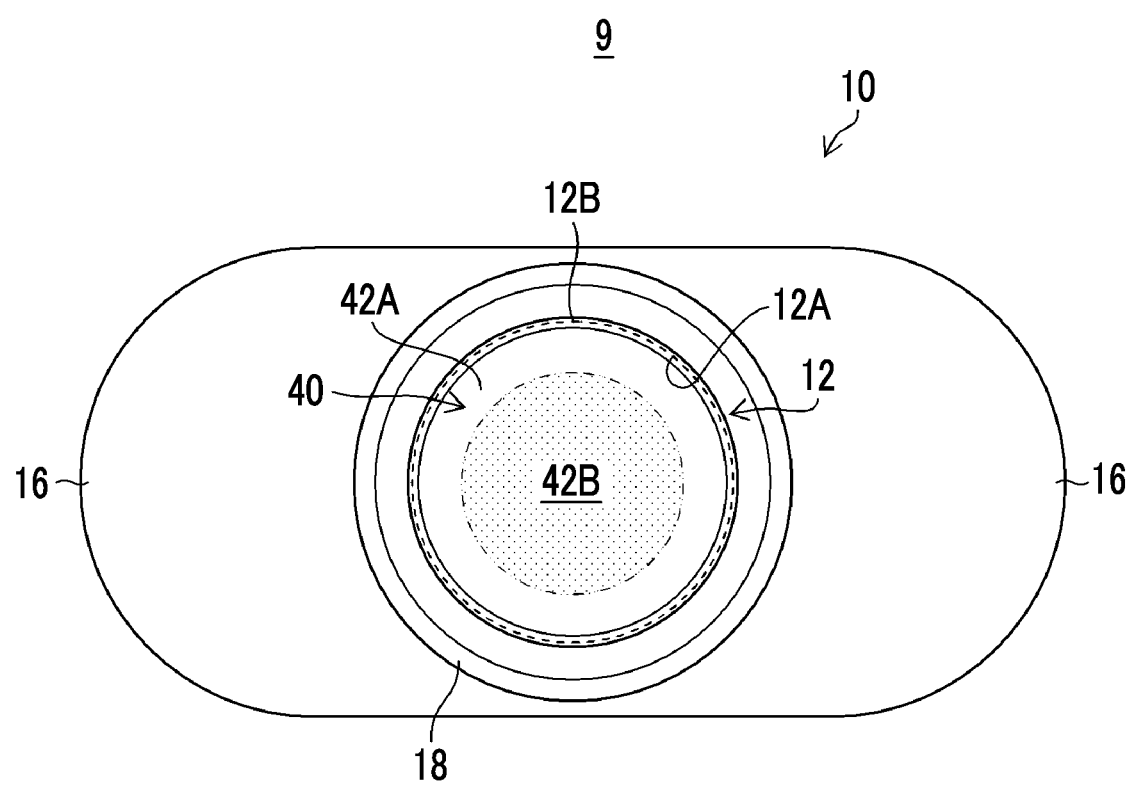
FIG. 26 is a view illustrating a microneedle array unit in a ninth form as seen from the opening of the container.

FIG. 24 is a view illustrating microneedle array units 5 and 6 in fifth and sixth forms as seen from the opening 12A of the container 10, and FIG. 25 is a view illustrating microneedle array units 7 and 8 in seventh and eighth forms as seen from the opening 12A of the container 10. FIG. 26 is a view illustrating a microneedle array unit 9 in a ninth form as seen from the opening 12A of the container 10.

The configurations which are the same as those of the microneedle array unit 1 are denoted by the same reference numerals, and the description thereof will not be provided.

As illustrated in FIG. 24, a difference between the microneedle array unit 5 and the microneedle array unit 1 is the shape of the flange portion 16. The microneedle array unit 5 has a rectangular shape. Further, a difference between the microneedle array unit 6 and the microneedle array unit 1 is the shape of the flange portion 16. The microneedle array unit 6 has a square shape.

As illustrated in FIG. 25, a difference between the microneedle array unit 7 and the microneedle array unit 1 is the shape of the flange portion 16. The microneedle array unit 7 has a circular shape. Further, a difference between the microneedle array unit 7 and the microneedle array unit 1 is the shape of the flange portion 16. The microneedle array unit 7 has a polygonal shape, which is a hexagon.

The microneedle array units 5, 6, 7, and 8 having the flange portions 16 in shapes different from one another can exert the same effects as those of the microneedle array unit 1. The microneedle array units 5, 6, 7, and 8 having the flange portions 16 in shapes different from one another can also be produced by performing the same steps as those for the microneedle array unit 1.

Basically, the flange portions 16 are attached to the skin. In a case where the shapes of the flange portions 16 are different from one another, this means that the areas where the flange portions 16 are in contact with the skin are different from one another.

It is preferable to select the container 10 that includes the flange portion 16 in an appropriate shape in consideration of the location where the skin is punctured by the microneedle array 40 or the like.

Further, FIG. 24 and FIG. 25 illustrate a plurality of flange portions 16 having shapes different from one another, but the shapes are not limited thereto.

As illustrated in FIG. 26, a difference between the microneedle array unit 9 and the microneedle array unit 1 is the shape of the protrusion 12B. In the microneedle array unit 9, the protrusion 12B is continuously provided along the outer surface of the accommodating portion 12. One continuous protrusion 12B supports the outer peripheral surface 42A of the microneedle array 40.

Figure 27:
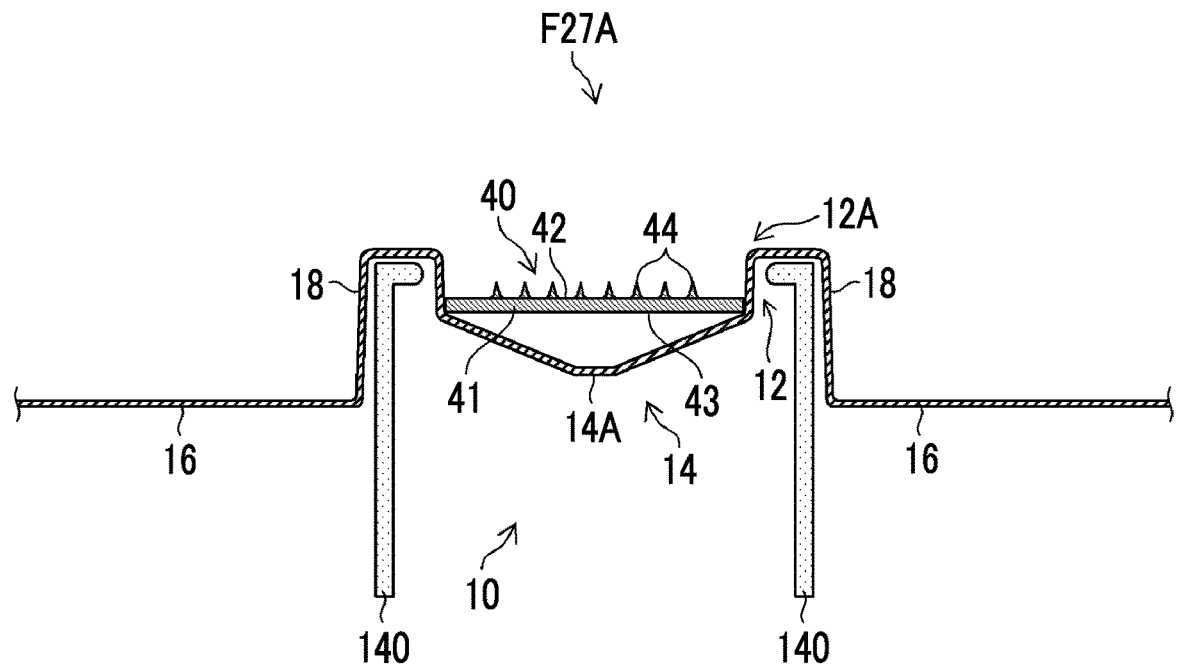
FIG. 27 is another step view illustrating the method of producing the microneedle array unit.
Figure 27:
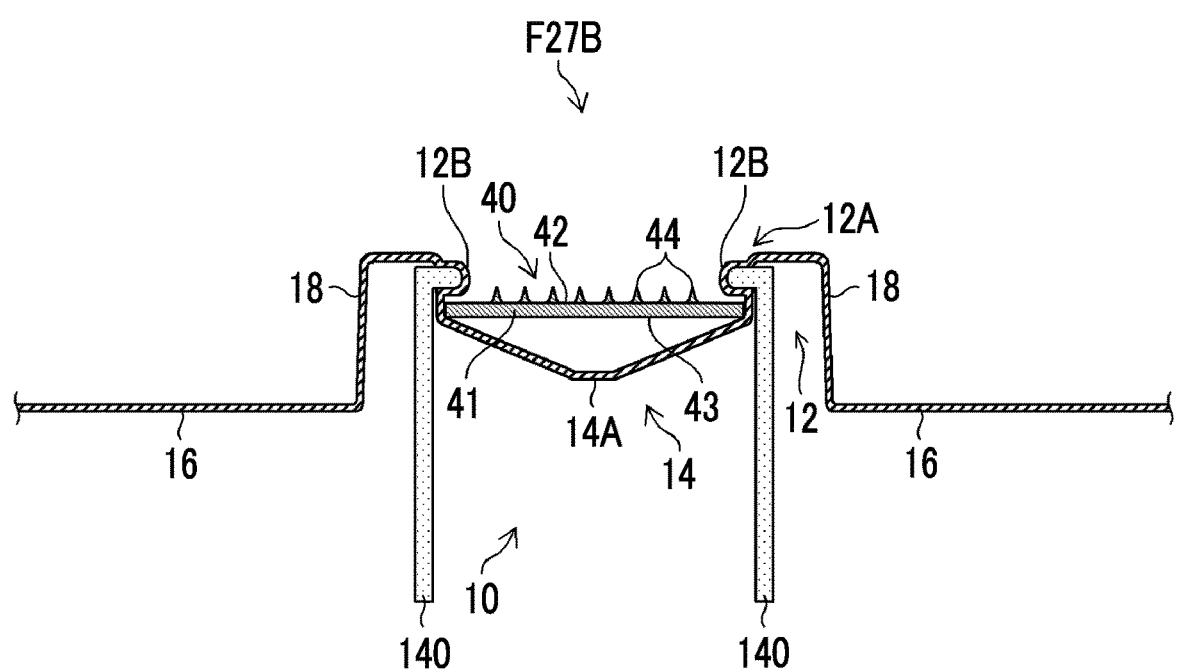

A case of producing the microneedle array unit 9 will be described with reference to FIG. 27. As shown by F27A, the container 10 is provided by allowing the opening 12A of the accommodating portion 12 to face upward. Next, the microneedle array 40 is accommodated in the container 10 in a state in which the needles 44 of the microneedle array 40 are allowed to face upward. As shown by F27B, the protrusions 12B can be formed on the entire circumference of the outer surface of the accommodating portion 12 by deforming the outer surface of the accommodating portion 12 inward using the pressing jig 140. The case where the protrusions 12B are formed on the entire circumference of the outer surface of the accommodating portion 12 has been described, but the production method illustrated in FIG. 27 can be applied even in a case of forming a plurality of protrusions 12B in the first to eighth aspects.

EXPLANATION OF REFERENCES

1: microneedle array unit
2: microneedle array unit
3: microneedle array unit
4: microneedle array unit
5: microneedle array unit
6: microneedle array unit
7: microneedle array unit
8: microneedle array unit
9: microneedle array unit
10: container
12: accommodating portion
12A: opening
12B: protrusion
14: deformable portion
14A: vertex portion
16: flange portion
18: bent portion
20: flat plate
30: lid
32: bag
40: microneedle array
41: sheet
42: one surface
42A: outer peripheral surface
42B: microneedle region
42C: imaginary line
43: the other surface
44: needle
50: finger
60: skin
100: support
100A: opening
100B: wall portion
100C: notch
120: adsorption pad
140: pressing jig
200: driving device
210: Z-axis driving mechanism
220: X-Y axis driving mechanism

What is claimed is:

1. A method of producing a microneedle array unit, comprising:
    an array preparing step of preparing a microneedle array which includes a sheet and a plurality of needles arranged on one surface of the sheet;
    a container preparing step of preparing a container which includes an accommodating portion defining an opening and a space for accommodating the microneedle array, and a deformable portion disposed on a side opposite to the opening and integrated with the accommodating portion;
    an accommodating step of accommodating the microneedle array in the accommodating portion of the container by allowing the other surface of the sheet of the microneedle array and the deformable portion of the container to oppose each other; and
    a deforming step of deforming an outer peripheral surface of the accommodating portion inward to form at least one protrusion, which is configured between the one surface of the sheet of the microneedle array and the opening of the accommodating portion, to reduce an area of the opening of the accommodating portion.

2. The method of producing a microneedle array unit according to claim 1,
    wherein in the deforming step, two or more protrusions are formed.

3. The method of producing a microneedle array unit according to claim 1,
    wherein in the accommodating step, the one surface of the sheet of the microneedle array is supported by a support having a hollow structure that defines an opening from below in a non-contact manner with the plurality of needles.

4. The method of producing a microneedle array unit according to claim 3, wherein the support has a notch extending downward from the opening of the support, and a part of the support having the notch is accommodated in the container, and the outer peripheral surface of the accommodating portion is deformed inward toward the notch using a pressing jig in the deforming step.

5. The method of producing a microneedle array unit according to claim 1, wherein the microneedle array is accommodated in the container in a state in which the opening of the accommodating portion faces upward and the needles of the microneedle array face upward in the accommodating step, and the outer peripheral surface of the accommodating portion is deformed inward by a pressing jig in the deforming step.

6. The method of producing a microneedle array unit according to claim 4, wherein the pressing jig is heated.

7. The method of producing a microneedle array unit according to claim 3, wherein the microneedle array is sucked from the opening of the support.

8. The method of producing a microneedle array unit according to claim 1, wherein the accommodating step and the deforming step are performed in a sterile environment.

9. The method of producing a microneedle array unit according to claim 1, further comprising a sealing step of sealing the container after the deforming step.

10. The method of producing a microneedle array unit according to claim 9, wherein in the sealing step, the opening of the accommodating portion is sealed with a lid.

11. The method of producing a microneedle array unit according to claim 9, wherein in the sealing step, the container is put in a bag and sealed.

12. The method of producing a microneedle array unit according to claim 1, wherein the deforming step is performed after the accommodating step.

* * * * *